United States Patent
Evans et al.

(10) Patent No.: US 6,342,298 B1
(45) Date of Patent: Jan. 29, 2002

(54) MULTICOMPONENT SUPERABSORBENT FIBERS

(75) Inventors: Samantha J. Evans, Lymm Chesire; John A. Henderson, Birkenhead, both of (GB); Michael A. Mitchell, Lake Zurich; Anthony S. Tomlin, Island Lake, both of IL (US)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/273,878

(22) Filed: Mar. 22, 1999

Related U.S. Application Data

(63) Continuation-in-part of application No. 09/179,553, filed on Oct. 28, 1998, now Pat. No. 6,222,091, which is a continuation-in-part of application No. 09/120,674, filed on Jul. 22, 1998, now Pat. No. 6,235,965, which is a continuation-in-part of application No. 08/974,125, filed on Nov. 19, 1997, now Pat. No. 6,072,101.

(51) Int. Cl.[7] .................................................. D01F 8/00
(52) U.S. Cl. ........................ 428/373; 428/370; 428/374
(58) Field of Search ................................ 428/370, 373, 428/374

(56) References Cited

U.S. PATENT DOCUMENTS

| | | | |
|---|---|---|---|
| 3,041,292 A | 6/1962 | Hatch | 260/2.1 |
| 3,332,890 A | 7/1967 | Hatch | 260/2.1 |
| 3,645,922 A | 2/1972 | Weiss et al. | 260/2.1 R |

(List continued on next page.)

FOREIGN PATENT DOCUMENTS

| | | | |
|---|---|---|---|
| CA | 2066010 | 10/1992 | B01J/20/26 |
| DE | 43 33 056 | 3/1995 | C08F/8/00 |
| EP | 0 425 269 | 5/1991 | D01F/6/88 |
| EP | 0 700 672 | 3/1996 | A61F/13/15 |
| GB | 2269602 | 2/1994 | D21H/13/18 |
| WO | WO 95/22358 | 8/1995 | |
| WO | WO 96/15162 | 5/1996 | |
| WO | WO 96/15163 | 5/1996 | C08F/20/56 |
| WO | WO 96/15180 | 5/1996 | C08J/5/02 |
| WO | WO 96/17681 | 6/1996 | B01J/20/00 |
| WO | WO 97/43480 | 11/1997 | D06M/15/263 |
| WO | WO 98/24832 | 6/1998 | C08J/3/075 |
| WO | WO 98/37149 | 8/1998 | C08L/101/14 |

OTHER PUBLICATIONS

Bolto et al., "Further rapidly reacting ion–exchange resins," *J. Polymer Sci.*, Symposium No. 55, 87–94 (1976). (No month).

Zhang et al., *Nature*, 360, 142–144 (1992), (No month).

Salamone et al., *Polym. Mater. Sci. Eng.*, 55, 269–273 (1986), (No month).

McCormick et al., *Macromolecules*, 21, 694–699 (1988).

Bolto, *Polymeric Amines and Ammonium Salts*, Goethals, Ed., Paragon Press, New York, p. 365 (1979).

Bolto et al., *J. Polymer Sci.: Symposium Ser.*, 55, 95–104 (1976).

Badesso et al., *Hydrophilic Polymers; Performance with Environmental Acceptability*, Glass, Ed., American Chemical Society (1996).

St. Pierre et al., *Polym. Amines Ammonium Salts, Invited Lect. Contrib. Pap. Int. Symp.*, Goethals, Ed., p. 245 (1980), meeting date 1979.

Chang et al., *Macromolecules*, 20(3), 621–625 (1987).

Robeson, *J. App. Poly. Sci.*, 61, 1561–1569 (1996).

*Primary Examiner*—N. Edwards
(74) *Attorney, Agent, or Firm*—Marshall, Gerstein & Borun

(57) ABSTRACT

Multicomponent superabsorbent fibers are disclosed. The multicomponent fibers comprise at least one acidic water-absorbing resin and at least one basic water-absorbing resin. Each fiber contains at least one microdomain of the acidic resin in contact with, or in close proximity to, at least one microdomain of the basic resin. Blends of multicomponent superabsorbent fibers with particles of a second water-absorbing resin also are disclosed. Articles containing the multicomponent superabsorbent fibers also are disclosed.

22 Claims, 9 Drawing Sheets

U.S. PATENT DOCUMENTS

| | | | |
|---|---|---|---|
| 3,716,481 A | 2/1973 | Battaerd | 210/32 |
| 3,867,499 A | 2/1975 | Morgan | 264/182 |
| 3,901,236 A | 8/1975 | Assarsson | 128/284 |
| 3,957,698 A | 5/1976 | Hatch | 260/2.1 R |
| 4,139,499 A | 2/1979 | Wade et al. | 521/32 |
| 4,206,051 A | 6/1980 | Bolto et al. | 210/26 |
| 4,229,545 A | 10/1980 | Eppinger et al. | 521/38 |
| 4,378,439 A | 3/1983 | Pilkington | 521/26 |
| 4,578,068 A | 3/1986 | Kramer et al. | 604/368 |
| 4,685,909 A | 8/1987 | Berg et al. | 604/360 |
| 4,818,598 A | 4/1989 | Wong | 428/284 |
| 4,861,539 A | 8/1989 | Allen et al. | 264/204 |
| 4,913,869 A | 4/1990 | Funk | 264/182 |
| 4,962,172 A | 10/1990 | Allen et al. | 26/318.42 |
| 4,997,714 A | 3/1991 | Farrar et al. | 428/394 |
| 5,026,800 A | 6/1991 | Kimura et al. | 526/200 |
| 5,075,399 A | 12/1991 | Ahmed et al. | 526/287 |
| 5,079,080 A | 1/1992 | Schwarz | 428/288 |
| 5,085,787 A | 2/1992 | Pinschmidt, Jr. et al. | 252/8.551 |
| 5,147,956 A | 9/1992 | Allen | 526/318.42 |
| 5,162,074 A | 11/1992 | Hills | 156/644 |
| 5,274,018 A | 12/1993 | Tanaka et al. | 524/166 |
| 5,280,079 A | 1/1994 | Allen et al. | 525/329.2 |
| 5,340,865 A | 8/1994 | Neff et al. | 524/922 |
| 5,384,343 A | 1/1995 | Farrar et al. | 524/556 |
| 5,409,771 A | 4/1995 | Dahmen et al. | 428/327 |
| 5,447,727 A | 9/1995 | Graham | 424/487 |
| 5,547,745 A | 8/1996 | Hansen et al. | 428/283 |
| 5,667,743 A | 9/1997 | Tai et al. | 264/184 |
| 5,669,894 A | 9/1997 | Goldman et al. | 604/368 |
| 5,716,707 A | 2/1998 | Mukaida | 428/402 |
| 5,763,523 A | 6/1998 | Chen et al. | 524/922 |
| 5,804,605 A | 9/1998 | Palumbo | 521/28 |
| 5,849,862 A | 12/1998 | Davies et al. | 528/502 E |
| 6,150,495 A * | 11/2000 | Chou et al. | 528/328 |
| 6,174,602 B1 * | 1/2001 | Matsui et al. | 428/373 |
| 6,194,650 B1 * | 2/2001 | Chihani et al. | 604/366 |

* cited by examiner

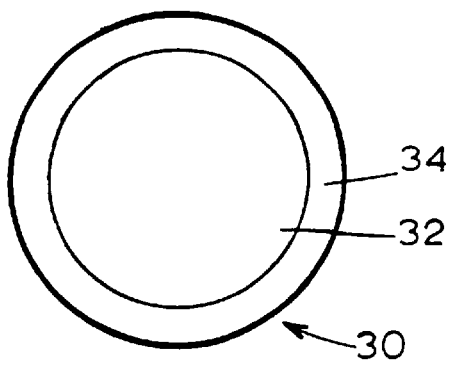 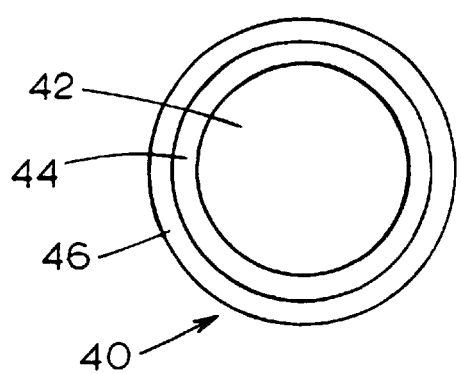
Fig. 3A  Fig. 3B
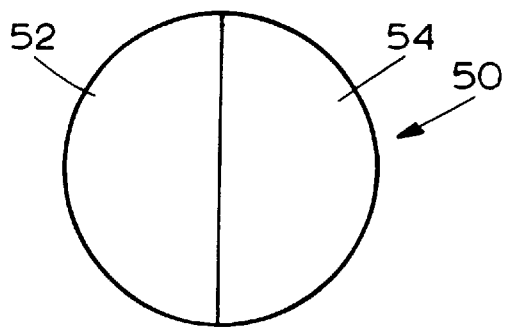
Fig. 4A
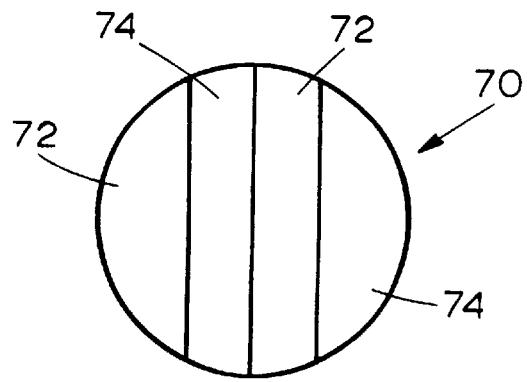
Fig. 4B

MULTICOMPONENT SUPERABSORBENT FIBERS

CROSS REFERENCE TO RELATED APPLICATIONS

This is a continuation-in-part application of U.S. patent application Ser. No. 09/179,553, filed Oct. 28, 1998, now U.S. Pat. No. 6,222,091, which is a continuation-in-part of U.S. patent application Ser. No. 09/120,674, filed Jul. 22, 1998, now U.S. Pat. No. 6,235,965, which is a continuation-in-part of U.S. patent application Ser. No. 08/974,125, filed Nov. 19, 1997, now U.S. Pat. No. 6,072,101.

FIELD OF THE INVENTION

The present invention relates to multicomponent superabsorbent particles, in fiber form, containing at least one acidic water-absorbing resin and at least one basic water-absorbing resin. Each multicomponent superabsorbent fiber has at least one microdomain of the acidic resin in contact with, or in close proximity to, at least one microdomain of the basic resin. The present invention also relates to mixtures containing (a) multicomponent superabsorbent fibers, and (b) particles of an acidic water-absorbing resin, a basic water-absorbing resin, or a mixture thereof.

BACKGROUND OF THE INVENTION

Water-absorbing resins are widely used in sanitary goods, hygienic goods, wiping cloths, water-retaining agents, dehydrating agents, sludge coagulants, disposable towels and bath mats, disposable door mats, thickening agents, disposable litter mats for pets, condensation-preventing agents, and release control agents for various chemicals. Water-absorbing resins are available in a variety of chemical forms, including substituted and unsubstituted natural and synthetic polymers, such as hydrolysis products of starch acrylonitrile graft polymers, carboxymethylcellulose, crosslinked polyacrylates, sulfonated polystyrenes, hydrolyzed polyacrylamides, polyvinyl alcohols, polyethylene oxides, polyvinylpyrrolidones, and polyacrylonitriles.

Such water-absorbing resins are termed "superabsorbent polymers," or SAPs, and typically are lightly crosslinked hydrophilic polymers. SAPs are generally discussed in Goldman et al. U.S. Pat. Nos. 5,669,894 and 5,559,335, the disclosures of which are incorporated herein by reference. SAPs can differ in their chemical identity, but all SAPs are capable of absorbing and retaining amounts of aqueous fluids equivalent to many times their own weight, even under moderate pressure. For example, SAPs can absorb one hundred times their own weight, or more, of distilled water. The ability to absorb aqueous fluids under a confining pressure is an important requirement for an SAP used in a hygienic article, such as a diaper.

As used here and hereafter, the term "SAP particles" refers to superabsorbent polymer particles in the dry state, i.e., particles containing from no water up to an amount of water less than the weight of the particles. The terms "SAP gel" or "SAP hydrogel" refer to a superabsorbent polymer in the hydrated state, i.e., particles that have absorbed at least their weight in water, and typically several times their weight in water. The SAP particles disclosed herein are in fiber form.

The dramatic swelling and absorbent properties of SAPs are attributed to (a) electrostatic repulsion between the charges along the polymer chains, and (b) osmotic pressure of the counter ions. It is known, however, that these absorption properties are drastically reduced in solutions containing electrolytes, such as saline, urine, and blood. The polymers function much less effectively in the presence of such physiologic fluids.

The decreased absorbency of electrolyte-containing liquids is illustrated by the absorption properties of a typical, commercially available SAP, i.e., sodium polyacrylate, in deionized water and in 0.9% by weight sodium chloride (NaCl) solution. The sodium polyacrylate can absorb 146.2 grams (g) of deionized water per gram of SAP (g/g) at 0 psi, 103.8 g of deionized water per gram of polymer at 0.28 psi, and 34.3 g of deionized water per gram of polymer of 0.7 psi. In contrast, the same sodium polyacrylate is capable of absorbing only 43.5 g, 29.7 g, and 24.8 g of 0.9% aqueous NaCl at 0 psi, 0.28 psi, and 0.7 psi, respectively. The absorption capacity of SAPs for body fluids, such as urine or menses, therefore, is dramatically lower than for deionized water because such fluids contain electrolytes. This dramatic decrease in absorption is termed "salt poisoning."

The salt poisoning effect has been explained as follows. Water-absorption and water-retention characteristics of SAPs are attributed to the presence of ionizable functional groups in the polymer structure. The ionizable groups typically are carboxyl groups, a high proportion of which are in the salt form when the polymer is dry, and which undergo dissociation and salvation upon contact with water. In the dissociated state, the polymer chain contains a plurality of functional groups having the same electric charge and, thus, repel one another. This electronic repulsion leads to expansion of the polymer structure, which, in turn, permits further absorption of water molecules. Polymer expansion, however, is limited by the crosslinks in the polymer structure, which are present in a sufficient number to prevent solubilization of the polymer.

It is theorized that the presence of a significant concentration of electrolytes interferes with dissociation of the ionizable functional groups, and leads to the "salt poisoning" effect. Dissolved ions, such as sodium and chloride ions, therefore, have two effects on SAP gels. The ions screen the polymer charges and the ions eliminate the osmotic imbalance due to the presence of counter ions inside and outside of the gel. The dissolved ions, therefore, effectively convert an ionic gel into a nonionic gel, and swelling properties are lost.

The most commonly used SAP for absorbing electrolyte-containing liquids, such as urine, is neutralized polyacrylic acid, i.e., containing at least 50%, and up to 100%, neutralized carboxyl groups. Neutralized polyacrylic acid, however, is susceptible to salt poisoning. Therefore, to provide an SAP that is less susceptible to salt poisoning, either an SAP different from neutralized polyacrylic acid must be developed, or the neutralized polyacrylic acid must be modified or treated to at least partially overcome the salt poisoning effect.

The removal of ions from electrolyte-containing solutions is often accomplished using ion exchange resins. In this process, deionization is performed by contacting an electrolyte-containing solution with two different types of ion exchange resins, i.e., an anion exchange resin and a cation exchange resin. The most common deionization procedure uses an acidic resin (i.e., cation exchange) and a basic resin (i.e., anion exchange). The two-step reaction for deionization is illustrated with respect to the desalinization of water as follows:

$$NaCl + R\text{—}SO_3H \rightarrow R\text{—}SO_3Na + HCl$$

$$HCl + R\text{—}N(CH_3)_3OH \rightarrow R\text{—}N(CH_3)_3Cl + H_2O.$$

The acidic resin (R—SO$_3$H) removes the sodium ion; and the basic resin (R—N(CH$_3$)$_3$OH) removes the chloride ions. This ion exchange reaction, therefore, produces water as sodium chloride is adsorbed onto the resins. The resins used in ion exchange do not absorb significant amounts of water.

The most efficient ion exchange occurs when strong acid and strong base resins are employed. However, weak acid and weak base resins also can be used to deionize saline solutions. The efficiency of various combinations of acid and base exchange resins are as follows:

Strong acid—strong base (most efficient)
Weak acid—strong base
Strong acid—weak base
Weak acid—weak base (least efficient).

The weak acid/weak base resin combination requires that a "mixed bed" configuration be used to obtain deionization. The strong acid/strong base resin combination does not necessarily require a mixed bed configuration to deionize water. Deionization also can be achieved by sequentially passing the electrolyte-containing solution through a strong acid resin and strong base resin.

A "mixed bed" configuration of the prior art is a physical mixture of an acid ion exchange resin and a base ion exchange resin in an ion exchange column, as disclosed in Battaerd U.S. Pat. No. 3,716,481. Other patents directed to ion exchange resins having one ion exchange resin imbedded in a second ion exchange resin are Hatch U.S. Pat. No. 3,957,698, Wade et al. U.S. Pat. No. 4,139,499, Eppinger et al. U.S. Pat. No. 4,229,545, and Pilkington U.S. Pat. No. 4,378,439. Composite ion exchange resins also are disclosed in Hatch U.S. Pat. Nos. 3,041,092 and 3,332,890, and Weiss U.S. Pat. No. 3,645,922.

The above patents are directed to nonswelling resins that can be used to remove ions from aqueous fluids, and thereby provide purified water. Ion exchange resins used for water purification must not absorb significant amounts of water because resin swelling resulting from absorption can lead to bursting of the ion exchange containment column.

Ion exchange resins or fibers also have been disclosed for use in absorbent personal care devices (e.g., diapers) to control the pH of fluids that reach the skin, as set forth in Berg et al., U.S. Pat. No. 4,685,909. The ion exchange resin is used in this application to reduce diaper rash, but the ion exchange resin is not significantly water absorbent and, therefore, does not improve the absorption and retention properties of the diaper.

Ion exchange resins having a composite particle containing acid and base ion exchange particles embedded together in a matrix resin, or having acid and base ion exchange particles adjacent to one another in a particle that is free of a matrix resin are disclosed in B. A. Bolto et al., *J. Polymer Sci. :Symposium No. 55*, John Wiley and Sons, Inc. (1976), pages 87–94. The Bolto et al. publication is directed to improving the reaction rates of ion exchange resins for water purification and does not utilize resins that absorb substantial amounts of water.

Other investigators have attempted to counteract the salt poisoning effect and thereby improve the performance of SAPs with respect to absorbing electrolyte-containing liquids, such as menses and urine. For example, Tanaka et al. U.S. Pat. No. 5,274,018 discloses an SAP composition comprising a swellable hydrophilic polymer, such as polyacrylic acid, and an amount of an ionizable surfactant sufficient to form at least a monolayer of surfactant on the polymer. In another embodiment, a cationic gel, such as a gel containing quaternized ammonium groups and in the hydroxide (i.e., OH) form, is admixed with an anionic gel (i.e., a polyacrylic acid) to remove electrolytes from the solution by ion exchange. Quaternized ammonium groups in the hydroxide form are very difficult and time-consuming to manufacture, thereby limiting the practical use of such cationic gels.

Wong U.S. Pat. No. 4,818,598 discloses the addition of a fibrous anion exchange material, such as DEAE (diethylaminoethyl) cellulose, to a hydrogel, such as a polyacrylate, to improve absorption properties. The ion exchange resin "pretreats" the saline solution (e.g., urine) as the solution flows through an absorbent structure (e.g., a diaper). This pretreatment removes a portion of the salt from the saline. The conventional SAP present in the absorbent structure then absorbs the treated saline more efficiently than untreated saline. The ion exchange resin, per se, does not absorb the saline solution, but merely helps overcome the "salt poisoning" effect.

WO 96/17681 discloses admixing discrete anionic SAP particles, such as polyacrylic acid, with discrete polysaccharide-based cationic SAP particles to overcome the salt poisoning effect. Similarly, WO 96/15163 discloses combining a cationic SAP having at least 20% of the functional groups in a basic (i.e., OH) form with a cationic exchange resin, i.e., a nonswelling ion exchange resin, having at least 50% of the functional groups in the acid form. WO 96/15180 discloses an absorbent material comprising an anionic SAP, e.g., a polyacrylic acid and an anion exchange resin, i.e., a nonswelling ion exchange resin.

SAP particles in fiber form are known. For example, Allen U.S. Pat. No. 5,147,956 and Allen et al. U.S. Pat. Nos. 4,962,172; 4,861,539; and 4,280,079 disclose absorbent products and their method of manufacture. Farrar et al. U.S. Pat. No. 4,997,714 also discloses absorbent products in a fiber form, and their method of manufacture. Additional patents include Morgan U.S. Pat. No. 3,867,499, Funk U.S. Pat. No. 4,913,869, and Tai et al. U.S. Pat. No. 5,667,743. GB 2,269,602 discloses a wet-laid nonwoven fabric comprising a blend of SAP fibers and a less absorbing fiber, like woodpulp. European Patent Application 0 425 269 discloses a melt spun fiber containing a conventional synthetic material and an SAP. WO 98/24832 discloses an absorbent composition containing an acidic and basic material. The absorbent composition can be in a fiber form. Further patents directed to fibers include WO 96/JP651, WO 97/43480, and Hills U.S. Pat. No. 5,162,074.

Various references disclose combinations that attempt to overcome the salt poisoning effect. However, the references do not teach SAP fibers having the improved fluid absorption and retention properties, or absorption kinetics, demonstrated by the fibers of the present invention, which comprise at least one microdomain of an acidic resin in contact, or in close proximity, with at least one microdomain of a basic resin. These references also do not teach a mixture of resin particles wherein one component of the mixture is fibers of a multicomponent SAP.

The present invention, therefore, is directed to discrete SAP fibers that exhibit exceptional water absorption and retention properties, especially with respect to electrolyte-containing liquids, and thereby overcome the salt poisoning effect. In addition, the discrete SAP fibers have an ability to absorb liquids quickly, demonstrate good fluid permeability and conductivity into and through the SAP fiber, and have a high gel strength such that the hydrogel formed from the SAP fibers does not deform or flow under an applied stress or pressure, when used alone or in a mixture with other water-absorbing resins.

SUMMARY OF THE INVENTION

The present invention is directed to multicomponent SAPs, in fiber form, comprising at least one acidic water-absorbing resin, such as a polyacrylic acid, and at least one basic water-absorbing resin, such as a poly(vinylamine), a polyethyleneimine, or a poly(dialkylaminoalkyl acrylamide) or a poly(dialkylaminoalkyl methacrylamide), hereafter collectively referred to as poly(dialkylaminoalkyl(meth) acrylamides).

More particularly, the present invention is directed to multicomponent SAP fibers containing at least one discrete microdomain of at least one acidic water-absorbing resin in contact with, or in close proximity to, at least one microdomain of at least one basic water-absorbing resin. The acidic resin can be a strong or a weak acidic resin. Similarly, the basic resin can be a strong or a weak basic resin.

A preferred SAP contains one or more microdomains of at least one weak acidic resin and one or more microdomains of at least one weak basic resin. The properties demonstrated by such preferred multicomponent SAP particles are unexpected because, in ion exchange applications, the combination of a weak acid and a weak base is the least effective of any combination of a strong or weak acid ion exchange resin with a strong or weak basic ion exchange resin.

The multicomponent SAP fibers can contain a plurality of microdomains of the acidic water-absorbing resin and/or the basic water-absorbing resin dispersed throughout the particle. Alternatively, the multicomponent SAP fibers can be in the form of a core and sheath, wherein the core is a microdomain of a first water-absorbing resin and the sheath is a microdomain of a second water-absorbing resin. The multicomponent SAP fibers also can be in the form of a fiber of an acidic water-absorbing resin and a fiber of a basic water-absorbing resin that are twisted together in the form of a braid or rope.

Accordingly, one aspect of the present invention is to provide SAP fibers that have a high absorption rate, have good permeability and gel strength, overcome the salt poisoning effect, and demonstrate an improved ability to absorb and retain electrolyte-containing liquids, such as saline, blood, urine, and menses. The present SAP fibers contain discrete microdomains of acidic and basic resin, and during hydration, the fibers resist coalescence but remain fluid permeable.

Another aspect of the present invention is to provide an SAP having improved absorption and retention properties compared to a conventional SAP, such as sodium polyacrylate. The present multicomponent SAP fibers are produced by any method that positions a microdomain of an acidic water-absorbing resin in contact with, or in close proximity to, a microdomain of a basic water-absorbing resin to provide a discrete particle. Such SAP particles demonstrate improved absorption and retention properties, and permeability through and between particles compared to SAP compositions comprising a simple admixture of acidic resin particles and basic resin particles.

In one embodiment, the SAP fibers are produced by coextruding an acidic water-absorbing hydrogel and a basic water-absorbing hydrogel to provide multicomponent SAP fibers having a plurality of discrete microdomains of an acidic resin and a basic resin dispersed throughout the particle. In another embodiment, the present multicomponent SAP fibers can be prepared by admixing dry particles of a basic resin with a hydrogel of an acidic resin, then extruding the resulting mixture to form multicomponent SAP fibers having microdomains of a basic resin dispersed throughout a continuous phase of an acidic resin. Alternatively, dry acidic resin particles can be admixed with a basic resin hydrogel, followed by extruding the resulting mixture to form multicomponent SAP fibers having microdomains of an acidic resin dispersed in a continuous phase of a basic resin.

In addition, a multicomponent SAP fiber containing microdomains of an acidic resin and a basic resin dispersed in a continuous phase of a matrix resin can be prepared by adding dry particles of the acidic resin and dry particles of the basic resin to a hydrogel of the matrix hydrogel, then extruding.

In other embodiments, the acidic and basic water-absorbing hydrogels are coextruded, or spun, to form a fiber having a core-sheath configuration. Alternatively, the acidic and basic water-absorbing hydrogels are extruded, or spun, individually, then twisted together, in the form of a braid, to provide a multicomponent SAP fiber.

In accordance with yet another important aspect of the present invention, the acidic and basic resins are lightly crosslinked, such as with a suitable polyfunctional vinyl polymer. In preferred embodiments, the acidic resin, the basic resin, and/or the entire multicomponent SAP fiber are surface treated or annealed to further improve water absorption and retention properties, especially under a load.

Yet another important feature of the present invention is to provide an SAP fiber containing at least one microdomain of a weak acidic water-absorbing resin in contact with at least one microdomain of a weak basic water-absorbing resin.

An example of a weak acidic resin is polyacrylic acid having 0% to 25% neutralized carboxylic acid groups (i.e., DN=0 to DN=25). Examples of weak basic water-absorbing resins are a poly(vinylamine), a polyethylenimine, and a poly(dialkylaminoalkyl (meth) acrylamide) prepared from a monomer either having the general structure formula (I)

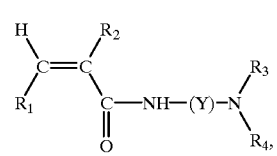

(I)

or the ester analog of (I) having the general structure formula (II)

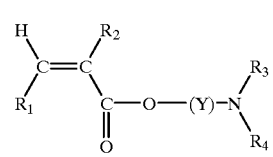

(II)

wherein $R_1$ and $R_2$, independently, are selected from the group consisting of hydrogen and methyl, Y is a divalent straight chain or branched organic radical having 1 to 8 carbon atoms, and $R_3$ and $R_{41}$, independently, are alkyl radicals having 1 to 4 carbon atoms. Examples of a strong basic water-absorbing resin are poly(vinylguanidine) and poly(allylguanidine).

Yet another aspect of the present invention is to provide an improved SAP material comprising a combination containing (a) multicomponent SAP fibers, and (b) particles of a second water-absorbing resin selected from the group consisting of an acidic water-absorbing resin, a basic water-absorbing resin, and a mixture thereof. The combination contains about 10% to about 90%, by weight, multicomponent SAP fibers and about 10% to about 90%, by weight, particles of the second water-absorbing resin.

Another important aspect of the present invention is to provide a method of continuously producing core-sheath multicomponent SAP fibers. In one embodiment, a poly (vinylamine) core is prepared using a wet spinning method, which then is immediately directed to a solution containing poly(acrylic acid) and a crosslinker. The freshly spun poly (vinylamine) fiber, therefore, has a sheath of poly(acrylic acid) applied thereto.

Still another aspect of the present invention is to provide diapers having a core comprising multicomponent SAP fibers or an SAP material of the present invention. Other articles that can contain the multicomponent SAP fibers or an SAP material of the present invention include catamenial devices, adult incontinence products, and devices for absorbing saline and other ion-containing fluids.

These and other aspects and advantages of the present invention will become apparent from the following detailed description of the preferred embodiments.

BRIEF DESCRIPTION OF THE DRAWINGS

FIGS. 3A and 3B are cross-sectional views of a water-absorbing fiber having a core microdomain of a first resin surrounded by a sheath microdomain of a second resin;

FIGS. 4A and 4B are cross-sectional views of water-absorbing fibers having a microdomain of a first resin in contact with a microdomain of a second resin;

DETAILED DESCRIPTION OF THE PREFERRED EMBODIMENTS

The present invention is directed to multicomponent SAP particles, in fiber form, containing at least one microdomain of an acidic water-absorbing resin in close proximity to, and preferably in contact with, at least one microdomain of a basic water-absorbing resin. Each fiber particle contains one or more microdomains of an acidic resin and one or more microdomains of a basic resin. The microdomains can be distributed nonhomogeneously or homogeneously throughout each fiber particle.

Each multicomponent SAP fiber of the present invention contains at least one acidic water-absorbing resin and at least one basic water-absoring-resin. In one embodiment, the SAP fibers consist essentially of acidic resins and basic resins, and contain microdomains of the acidic and/or basic resins. In another embodiment, microdomains of the acidic and basic resins are dispersed in an absorbent matrix resin.

The multicomponent SAP particles of the present invention are in the shape of a fiber. It is important that substantially each SAP particle contain at least one microdomain of an acidic water-absorbing resin and at least one microdomain of a basic water-absorbing resin in close proximity to one another. Improved water absorption and retention, and improved fluid permeability through and between SAP particles, are observed as long as the acidic resin microdomain and the basic resin microdomain are in close proximity within the particle. In a preferred embodiment, the microdomains of acidic and basic resin are in contact.

In some embodiments, an idealized multicomponent SAP fiber of the present invention is analogous to a liquid emulsion wherein small droplets of a first liquid, i.e., the dispersed phase, are dispersed in a second liquid, i.e., the continuous phase. The first and second liquids are immiscible, and the first liquid, therefore, is homogeneously dispersed in the second liquid. The first liquid can be water or oil based, and conversely, the second liquid is oil or water based, respectively.

Figure 1:
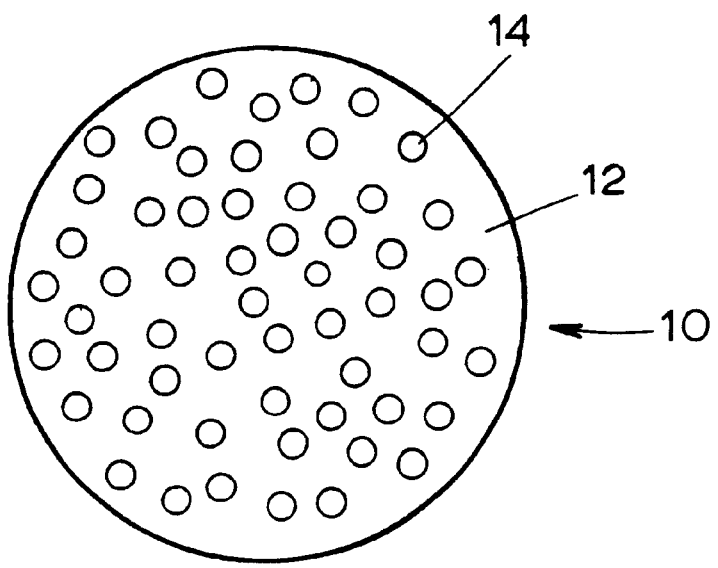
FIG. 1 is a cross-sectional view of a water-absorbing fiber containing microdomains of a first resin dispersed in a continuous phase of a second resin.

Therefore, in one embodiment, the multicomponent SAP fibers of the present invention can be envisioned as one or more microdomains of an acidic resin dispersed in a continuous phase of a basic resin, or as one or more microdomains of a basic resin dispersed in a continuous acid resin. These idealized multicomponent SAP fibers are illustrated in FIG. 1 showing a cross section of an SAP fiber 10 having discrete microdomains 14 of a dispersed resin in a continuous phase of a second resin 12. If microdomains 14 comprise an acidic resin, then continuous phase 12 comprises a basic resin. Conversely, if microdomains 14 comprise a basic resin, then continuous phase 12 is an acidic resin.

Figure 2:
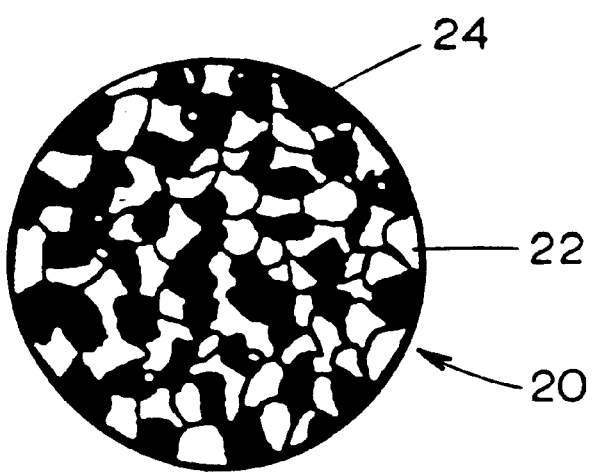
FIG. 2 is a cross-sectional view of a water-absorbing particle containing microdomains of a first resin and microdomains of a second resin dispersed throughout the particle.

In another embodiment, the SAP fibers are envisioned as microdomains of an acidic resin and microdomains of a basic resin dispersed throughout each particle, without a continuous phase. This embodiment is illustrated in FIG. 2, showing a cross section of an idealized multicomponent SAP fiber 20 having a plurality of microdomains of an acidic resin 22 and a plurality of microdomains of a basic resin 24 dispersed throughout fiber 20.

In yet another embodiment, microdomains of the acidic and basic resins are dispersed throughout a continuous phase comprising a matrix resin. This embodiment also is illustrated in FIG. 1 wherein multicomponent SAP fiber 10 contains one or more microdomains 14, each an acidic resin or a basic resin, dispersed in a continuous phase 12 of a matrix resin.

It should be understood that the microdomains within each fiber can be of regular or irregular shape, and that the microdomains can be dispersed homogeneously or nonhomogeneously throughout each particle. Accordingly, another important embodiment of the SAP fiber is illustrated in FIG. 3A, showing an idealized multicomponent fiber 30 having a core 32 of an acidic water-absorbing resin surrounded by a sheath 34 of a basic water-absorbing resin. Conversely, core 32 can comprise a basic resin, and sheath 34 can comprise an acidic resin.

FIG. 3B illustrates, in cross section, a similar embodiment having a core and concentric sheaths that alternate between sheaths of acidic resin and basic resin. In one embodiment, core 42 and sheath 46 comprise an acidic water-absorbing resin, and shell 44 comprises a basic water-absorbing resin. Other embodiments include: core 42 and sheath 46 comprising a basic resin and sheath 44 comprising an acidic resin, or core 42 comprising a matrix resin and sheaths 44 and 46 comprising an acidic resin and a basic resin in alternating shells. Other configurations are apparent to persons skilled in the art, such as increasing the number of shells around the core.

FIG. 4A illustrates another embodiment of the present SAP fibers, in cross section, wherein one microdomain 52 of an acidic water-absorbing resin is in contact with one microdomain 54 of a basic water-absorbing resin to provide a multicomponent SAP fiber 50. In this embodiment, a surface of an acidic resin is in contact with a surface of a microdomain of a basic resin. The embodiment illustrated in FIG. 4A extends to SAP fibers having more than one microdomain of each of the acidic resin and the basic resin, as illustrated in FIG. 4B, wherein, in cross section, multicomponent SAP fiber 70 contains alternating zones of acidic water-absorbing resin 72 and basic water-absorbing resin 74. Fiber 70 also can contain one or more layers 72 or 74 comprising a matrix resin.

Figure 5A:
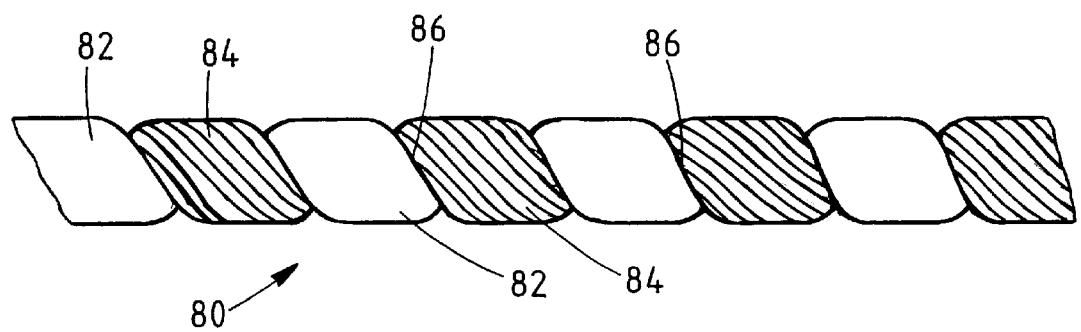
FIGS. 5A and 5B are schematic diagrams of a water-absorbing fiber having individual fibers of a first and a second water-absorbing resin twisted together to form a rope.

In another embodiment, the multicomponent SAP fiber comprises individual filaments of acidic resin and basic resin that are twisted together in the form of a rope. This embodiment is illustrated in FIGS. 5A and B, which illustrate a "twisted rope" embodiment of the present SAP fibers lengthwise and in cross section, respectively. In FIGS. 5A and B, a multicomponent SAP particle 80 comprises a filament 82 of acidic water-absorbing resin and a filament 84 of basic water-absorbing resin. Filaments 82 and 84 are in contact along zone of contact 86, thereby placing the acidic and basic resins in contact.

The "twisted rope" SAP fibers of FIGS. 5A and B also can be an embodiment wherein acidic resin filament 82 contains microdomains of a basic water-absorbing resin, i.e., is a multicomponent SAP fiber itself, and/or basic resin filament 84 contains microdomains of an acidic water-absorbing resin, i.e., also is a multicomponent SAP fiber itself. Filaments 82 and 84 then are intertwined to form multicomponent SAP fiber 80.

The embodiment of FIGS. 5A and B also can, be a filament 82 and/or a filament 84 comprising a matrix resin having microdomains of acidic resin and/or basic resin. In this embodiment, filament 82 contains microdomains of an acidic resin, or microdomains of an acidic and a basic resin, and filament 84 contains microdomains of a basic resin, or microdomains of an acidic resin and a basic resin.

The multicomponent SAP fibers of the present invention comprise an acidic resin and a basic resin in a weight ratio of about 95:5 to about 5:95, and preferably about 15:85 to about 85:15. To achieve the full advantage of the present invention, the weight ratio of acidic resin to basic resin in a multicomponent SAP fiber is about 30:70 to about 70:30. The acidic and basic resins can be distributed homogeneously or nonhomogeneously throughout the SAP fiber.

The present multicomponent SAP fibers contain at least about 50%, and preferably at least about 70%, by weight of acidic resin plus basic resin. To achieve the full advantage of the present invention, a multicomponent SAP fiber contains about 80% to 100% by weight of the acidic resin plus basic resin. Components of the present SAP fibers, other than the acidic and basic resin, typically, are matrix resins or other minor optional ingredients.

The multicomponent SAP fibers of the present invention can be of any cross-sectional geometry. The multicomponent SAP fibers can be prepared using an extrusion step. In such a case, the shape of the SAP fiber is determined by the shape of the extrusion die. The shape of the multicomponent SAP fibers also can be determined by other methods of preparing the particles, such wet or dry spinning, which are the preferred methods of preparation.

In accordance with the present invention, a microdomain is defined as a volume of an acidic resin or a basic resin that is present in a multicomponent SAP fiber. Because each multicomponent SAP particle contains at least one microdomain of an acidic resin, and at least one microdomain of a basic resin, a microdomain has a volume that is less than the volume of the multicomponent SAP fiber. A microdomain, therefore, can be as large as about 90% of the volume of multicomponent SAP fibers.

The multicomponent SAP fibers of the present invention are elongated, acicular SAP particles. The fiber can be in the shape of a cylinder, for example, having a minor dimension (i.e., diameter) and a major dimension (i.e., length). The fiber also can be in the form of a long filament that can be woven. Such filament-like fibers have a weight of below about 80 decitex, and preferably below about 70 decitex, per filament, for example, about 2 to about 60 decitex per filament. Tex is the weight in grams per one kilometer of fiber. One tex equals 10 decitex. For comparison, poly (acrylic acid) is about 0.78 decitex (0.078 tex), and poly (vinylamine) is about 6.1 decitex (0.61 tex).

Cylindrical multicomponent SAP fibers have a minor dimension (i.e., diameter of the fiber) less than about 1 mm, usually less than about 500 μm, and preferably less than 250 μm, down to about 10 μm. The cylindrical SAP fibers can have a relatively short major dimension, for example, about 1 mm, e.g., in a fibril, lamella, or flake-shaped article, but generally the fiber has a length of about 3 to about 100 mm. The filament-like fibers have a ratio of major dimension to minor dimension of at least 500 to 1, and preferably at least 1000 to 1, for example, up to and greater than 10,000 to 1.

Typically, a microdomain within a fiber or a filament of a fiber has a diameter of about 750 μm or less, and preferably about 100 μm or less. To achieve the full advantage of the present invention, a microdomain has a diameter of about 20 μm or less. The multicomponent SAP fibers also contain microdomains that have submicron diameters, e.g., microdomain diameters of less than 1 μm to about 0.01 μm. In other embodiments, the microdomain can be the entire filament of a twisted rope SAP fiber. Microdomains also can be the core and the sheath in the embodiments illustrated in FIGS. 3A and B.

Each multicomponent SAP fiber contains one or more microdomains of an acidic water-absorbing resin and one or more microdomains of a basic water-absorbing resin, either in contact or in close proximity to one another. As illustrated hereafter, the microdomain structure of the present SAP fibers provides improved fluid absorption (both in amount of fluid absorbed and retained, and rate of absorption) compared to an SAP comprising a simple mixture of discrete acidic SAP resin fibers and discrete basic SAP resin fibers. In accordance with another important feature of the present invention, the present multicomponent SAP fibers also demonstrate improved permeability, both through an individual fiber and between fibers. The present SAP fibers, therefore, have an improved ability to rapidly absorb a fluid, even in "gush" situations, for example, when used in diapers to absorb urine.

The features of good permeability, absorption and retention properties, especially of electrolyte-containing liquids, demonstrated by the present multicomponent SAP fibers, is important with respect to practical uses of an SAP. These improved properties are attributed, in part, to the fact that electrolyte removal from the liquid is facilitated by contacting a single particle (which, in effect, performs an essentially simultaneous deionization of the liquid), as opposed to the liquid having to contact individual acidic and basic particles (which, in effect, performs a sequential two-step deionization).

If a blend of acidic resin fibers and basic resin fibers is used, the fibers typically have a small particle size. A small particle size is required to obtain desirable desalination kinetics, because the electrolyte is removed in a stepwise manner, with the acidic resin removing the cation and the basic resin removing the anion. The electrolyte-containing fluid, therefore, must contact two particles for desalination, and this process is facilitated by small particle sized SAPs. Small particles, however, have the effect of reducing flow of the fluid through and between SAP particles, i.e., permeability is reduced and a longer time is required to absorb the fluid.

In addition, in practical use, such as in diapers, SAPs are used in conjunction with a cellulosic pulp. If a blend of acidic resin particles and basic resin particles is used as the SAP, the cellulosic pulp can cause a separation between the acidic resin particles and basic resin particles, which adversely affects desalination. The present multidomain SAP fibers overcome this problem because the acidic resin and basic resin are present in a single particle. The introduction of cellulosic pulp, therefore, cannot separate the acidic and basic resin and cannot adversely affect desalination by the SAP.

A single multicomponent SAP particle, like a present fiber, simultaneously desalinates an electrolyte-containing liquid. Desalination is essentially independent of particle size. Accordingly, the present multicomponent SAP fibers can be of a larger size. These features allow for improved liquid permeability through and between the SAP particles, and results in a more rapid absorption of the electrolyte-containing liquid.

The following schematic reactions illustrate the reactions which occur to deionize, e.g., desalinate, an aqueous saline solution, and that are performed essentially simultaneously in a single microcomposite SAP particle, but are performed stepwise in a simple mixture of acidic and basic resins:

R—$CO_2H$+NaCl→R—$CO_2^-$$Na^+$+HCl      (acidic resin)

R—$NH_2$+HCl→R—$NH_3^+$$Cl^-$      (basic resin)

The present multicomponent SAP fibers can be in a form wherein a microdomain of an acidic water-absorbing resin is in contact with a microdomain of a basic water-absorbing resin. In another embodiment, the SAP fibers can be in a form wherein at least one microdomain of an acidic water-absorbing resin is dispersed in a continuous phase of a basic water-absorbing resin. Alternatively, the multicomponent SAP fibers can be in a form wherein at least one microdomain of a basic resin is dispersed in a continuous phase of an acidic resin. In another embodiment, at least one microdomain of one or more acidic resin and at least one microdomain of one or more basic resin comprise the entire SAP fiber, and neither type of resin is considered the dispersed or the continuous phase. In yet another embodiment, at least one microdomain of an acidic resin and at least one microdomain of a basic resin are dispersed in a matrix resin.

An acidic water-absorbing resin present in a multicomponent SAP fiber can be either a strong or a weak acidic water-absorbing resin. The acidic water-absorbing resin can be a single resin, or a mixture of resins. The acidic resin can be a homopolymer or a copolymer. The identity of the acidic water-absorbing resin is not limited as long as the resin is capable of swelling and absorbing at least ten times its weight in water, when in a neutralized form. The acidic resin is present in its acidic form, i.e., about 75% to 100% of the acidic moieties are present in the free acid form. As illustrated hereafter, although the free acid form of a acidic water-absorbing resin is generally a poor water absorbent, the combination of an acidic resin and a basic resin in a present multicomponent SAP fiber provides excellent water absorption and retention properties.

The acidic water-absorbing resin typically is a lightly crosslinked acrylic-type resin, such as lightly crosslinked polyacrylic acid. The lightly crosslinked acidic resin typically is prepared by polymerizing an acidic monomer containing an acyl moiety, e.g., acrylic acid, or a moiety capable of providing an acid group, i.e., acrylonitrile, in the presence of a crosslinker, i.e., a polyfunctional organic compound. The acidic resin can contain other copolymerizable units, i.e., other monoethylenically unsaturated comonomers, well known in the art, as long as the polymer is substantially, i.e., at least 10%, and preferably at least 25%, acidic monomer units. To achieve the full advantage of the present invention, the acidic resin contains at least 50%, and more preferably, at least 75%, and up to 100%, acidic monomer units. The other copolymerizable units can, for example, help improve the hydrophilicity and crosslinking of the polymer.

Ethylenically unsaturated carboxylic acid and carboxylic acid anhydride monomers useful in the acidic water-absorbing resin include acrylic acid, methacrylic acid, ethacrylic acid, α-chloroacrylic acid, α-cyanoacrylic acid, β-methylacrylic acid (crotonic acid), α-phenylacrylic acid, β-acryloxy-propionic acid, sorbic acid, α-chlorosorbic acid, angelic acid, cinnamic acid, p-chlorocinnamic acid, β-stearylacrylic acid, itaconic acid, citraconic acid, mesaconic acid, glutaconic acid, aconitic acid, maleic acid, fumaric acid, tricarboxyethylene, and maleic anhydride.

Ethylenically unsaturated sulfonic acid monomers include aliphatic or aromatic vinyl sulfonic acids, such as vinylsulfonic acid, allyl sulfonic acid, vinyl toluene sulfonic acid, styrene sulfonic acid, acrylic and methacrylic sulfonic acids, such as sulfoethyl acrylate, sulfoethyl methacrylate, sulfopropyl acrylate, sulfopropyl methacrylate, 2-hydroxy-3-methacryloxypropyl sulfonic acid, and 2-acrylamide-2-methylpropane sulfonic acid.

As set forth above, polymerization of acidic monomers, and copolymerizable monomers, if present, most commonly is performed by free radical processes in the presence of a polyfunctional organic compound. The acidic resins are crosslinked to a sufficient extent such that the polymer is water insoluble. Crosslinking renders the acidic resins substantially water insoluble, and, in part, serves to determine the absorption capacity of the resins. For use in absorption applications, an acidic resin is lightly crosslinked, i.e., has a crosslinking density of less than about 20%, preferably less than about 10%, and most preferably about 0.01% to about 7%.

A crosslinking agent most preferably is used in an amount of less than about 7 wt %, and typically about 0.1 wt % to about 5 wt %, based on the total weight of monomers. Examples of crosslinking polyvinyl monomers include, but are not limited to, polyacrylic (or polymethacrylic) acid esters represented by the following formula (III); and bisacrylamides, represented by the following formula (IV).

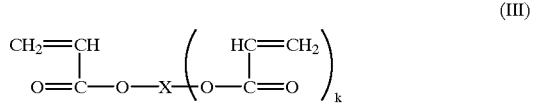
(III)

wherein x is ethylene, propylene, trimethylene, cyclohexyl, hexamethylene, 2-hydroxypropylene, —(CH$_2$CH$_2$O)$_n$CH$_2$CH$_2$—, or

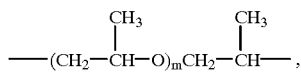

n and m are each an integer 5 to 40, and k is 1 or 2;

(IV)

wherein 1 is 2 or 3.

The compounds of formula (III) are prepared by reacting polyols, such as ethylene glycol, propylene glycol, trimethylolpropane, 1,6-hexanediol, glycerin, pentaerythritol, polyethylene glycol, or polypropylene glycol, with acrylic acid or methacrylic acid. The compounds of formula (IV) are obtained by reacting polyalkylene polyamines, such as diethylenetriamine and triethylenetetramine, with acrylic acid.

Specific crosslinking monomers include, but are not limited to, 1,4-butanediol diacrylate, 1,4-butanediol dimethacrylate, 1,3-butylene glycol diacrylate, 1,3-butylene glycol dimethacrylate, diethylene glycol diacrylate, diethylene glycol dimethacrylate, ethoxylated bisphenol A diacrylate, ethoxylated bisphenol A dimethacrylate, ethylene glycol dimethacrylate, 1,6-hexanediol diacrylate, 1,6-hexanediol dimethacrylate, neopentyl glycol dimethacrylate, polyethylene glycol diacrylate, polyethylene glycol dimethacrylate, triethylene glycol diacrylate, triethylene glycol dimethacrylate, tripropylene glycol diacrylate, tetraethylene glycol diacrylate, tetraethylene glycol dimethacrylate, dipentaerythritol pentaacrylate, pentaerythritol tetraacrylate, pentaerythritol triacrylate, trimethylolpropane triacrylate, trimethylolpropane trimethacrylate, tris(2-hydroxyethyl) -isocyanurate triacrylate, tris(2-hydroxyethyl)isocyanurate trimethacrylate, divinyl esters of a polycarboxylic acid, diallyl esters of a polycarboxylic acid, triallyl terephthalate, diallyl maleate, diallyl fumarate, hexamethylenebismaleimide, trivinyl trimellitate, divinyl adipate, diallyl succinate, a divinyl ether of ethylene glycol, cyclopentadiene diacrylate, tetraallyl ammonium halides, or mixtures thereof. Compounds such as divinylbenzene and divinyl ether also can be used to crosslink the poly(dialkylaminoalkyl acrylamides). Especially preferred crosslinking agents are N,N'-methylenebisacrylamide, N,N'-methylenebismethacrylamide, ethylene glycol dimethacrylate, and trimethylolpropane triacrylate.

The acidic resin, either strongly acidic or weakly acidic, can be any resin that acts as an SAP in its neutralized form. The acidic resins typically contain a plurality of carboxylic acid, sulfonic acid, phosphonic acid, phosphoric acid, and/or sulfuric acid moieties. Examples of acidic resins include, but are not limited to, polyacrylic acid, hydrolyzed starch-acrylonitrile graft copolymers, starch-acrylic acid graft copolymers, saponified vinyl acetate-acrylic ester copolymers, hydrolyzed acrylonitrile copolymers, hydrolyzed acrylamide copolymers, ethylene-maleic anhydride copolymers, isobutylene-maleic anhydride copolymers, poly(vinylsulfonic acid), poly(vinylphosphonic acid), poly(vinylphosphoric acid), poly(vinylsulfuric acid), sulfonated polystyrene, poly(aspartic acid), poly(lactic acid), and mixtures thereof. The preferred acidic resins are the polyacrylic acids.

The multicomponent SAP fibers can contain individual microdomains that: (a) contain a single acidic resin or (b) contain more than one, i.e., a mixture, of acidic resins. The multicomponent SAP fibers also can contain microdomains wherein, for the acidic component, a portion of the acidic microdomains comprise a first acidic resin or acidic resin mixture, and the remaining portion comprises a second acidic resin or acidic resin mixture.

Analogous to the acidic resin, the basic water-absorbing resin in the present SAP fibers can be a strong or weak basic water-absorbing resin. The basic water-absorbing resin can be a single resin or a mixture of resins. The basic resin can be a homopolymer or a copolymer. The identity of the basic resin is not limited as long as the basic resin is capable of swelling and absorbing at least 10 times its weight in water, when in a charged form. The weak basic resin typically is present in its free base, or neutral, form, i.e., about 75% to about 100% of the basic moieties, e.g., amino groups, are present in a neutral, uncharged form. The strong basic resins typically are present in the hydroxide (OH) or bicarbonate (HCO$_3$) form.

The basic water-absorbing resin typically is a lightly crosslinked acrylic type resin, such as a poly(vinylamine) or a poly(dialkylaminoalkyl (meth)acrylamide). The basic resin also can be a polymer such as a lightly crosslinked polyethylenimine, a poly(allylamine), a poly(allylguanidine), a poly(dimethyldiallylammonium hydroxide), a quaternized polystyrene derivative, such as

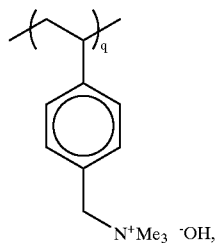

a guanidine-modified polystyrene, such as

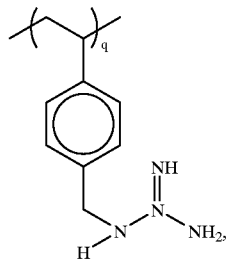

a quaternized poly((meth)acrylamide) or ester analog, such as

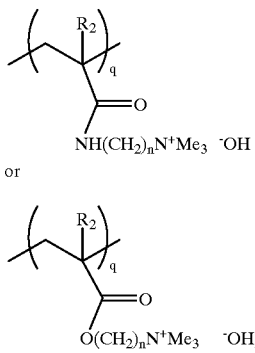

or wherein Me is methyl, $R_2$ is hydrogen or methyl, n is a number 1 to 8, and q is a number from in to about 100,000, or a poly(vinylguanidine), i.e., poly(VG), a strong basic water-absorbing resin having the general structural formula (V)

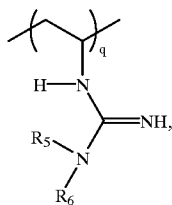

(V)

wherein q is a number from 10 to about 100,000, and $R_5$ and $R_6$, independently, are selected from the group consisting of hydrogen, $C_1$–$C_4$ alkyl, $C_3$–C6 cycloalkyl, benzyl, phenyl, alkyl-substituted phenyl, naphthyl, and similar aliphatic and aromatic groups. The lightly crosslinked basic water-absorbing resin can contain other copolymerizable units and is crosslinked using a polyfunctional organic compound, as set forth above with respect to the acidic water-absorbing resin.

A basic water-absorbing resin used in the present SAP fibers typically contains an amino or a guanidino group. Accordingly, a water-soluble basic resin also can be crosslinked in solution by suspending or dissolving an uncrosslinked basic resin in an aqueous or alcoholic medium, then adding a di- or polyfunctional compound capable of crosslinking the basic resin by reaction with the amino groups of the basic resin. Such crosslinking agents include, for example, multifunctional aldehydes (e.g., glutaraldehyde), multifunctional acrylates (e.g., butanediol diacrylate, TMPTA), halohydrins (e.g., epichlorohydrin), dihalides (e.g., dibromopropane), disulfonate esters (e.g., $ZA(O_2)O$—$(CH_2)_n$—$OS(O)_2Z$, wherein n is 1 to 10, and Z is ethyl or tosyl), multifunctional epoxies (e.g., ethylene glycol diglycidyl ether), multifunctional esters (e.g., dimethyl adipate), multifunctional acid halides (e.g., oxalyl chloride), multifunctional carboxylic acids (e.g., succinic acid), carboxylic acid anhydrides (e.g., succinic anhydride), organic titanates (e.g., TYZOR AA from DuPont), melamine resins (e.g., CYMEL 301, CYMEL 303, CYMEL 370, and CYMEL 373 from Cytec Industries, Wayne, N.J.), hydroxymethyl ureas (e.g., N,N'-dihydroxymethyl-4,5-dihydroxyethyleneurea), and multifunctional isocyanates (e.g., toluene diisocyanate or methylene diisocyanate).

Crosslinking agents also are disclosed in Pinschmidt, Jr. et al. U.S. Pat. No. 5,085,787, incorporated herein by reference, and in EP 450 923.

Conventionally, the crosslinking agent is water or alcohol soluble, and possesses sufficient reactivity with the basic resin such that crosslinking occurs in a controlled fashion, preferably at a temperature of about 25° C. to about 150° C. Preferred crosslinking agents are ethylene glycol diglycidyl ether (EGDGE), a water-soluble diglycidyl ether, and a dibromoalkane, an alcohol-soluble compound.

The basic resin, either strongly or weakly basic, therefore, can be any resin that acts as an SAP in its charged form. The basic resin typically contains amino or guanidino moieties. Examples of basic resins include a poly(vinylamine), a polyethylenimine, a poly(vinylguanidine), a poly (allylamine), a poly(allylguanidine), or a poly (dialkylaminoalkyl (meth)acrylamide) prepared by polymerizing and lightly crosslinking a monomer having the structure

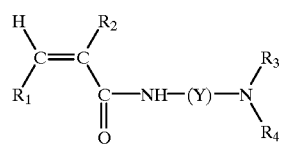

or its ester analog

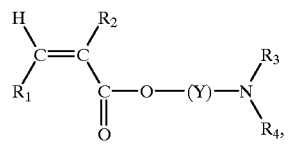

wherein $R_1$ and $R_2$, independently, are selected from the group consisting of hydrogen and methyl, Y is a divalent straight chain or branched organic radical having 1 to 8 carbon atoms, and $R_3$ and $R_4$, independently, are alkyl radicals having 1 to 4 carbon atoms. Preferred basic resins include a poly(vinylamine), polyethylenimine, poly (vinylguanidine), poly(dimethylaminoethyl acrylamide) (poly(DAEA)), and poly(dimethylaminopropyl methacrylamide) (poly(DMAPMA)). Analogous to microdomains of an acidic resin, the present multicomponent SAPs can contain microdomains of a single basic resin, microdomains containing a mixture of basic resins, or microdomains of different basic resins.

The present multicomponent SAP fibers can be prepared by various methods, and the method of preparing a multicomponent SAP fiber is not limited by the following embodiments. Any method that provides a fiber having at least one microdomain of an acidic resin in contact with or in close proximity to at least one microdomain of a basic resin is suitable.

In one method, dry particles of a basic resin, optionally surface crosslinked and/or annealed, are admixed into a rubbery gel of an acidic resin. The resulting mixture is extruded, then dried, and optionally surface crosslinked and/or annealed, to provide multicomponent SAP fibers having microdomains of a basic resin dispersed in a continuous phase of an acidic resin. Alternatively, particles of an acidic resin, optionally surface crosslinked and/or annealed, can be admixed into a rubbery gel of a basic resin, and the resulting mixture is extruded and dried, and optionally surface crosslinked and/or annealed, to provide multicomponent SAP fibers having microdomains of an acidic resin dispersed in a continuous phase of a basic resin.

In another method, dry particles of an acidic resin can be admixed with dry particles of a basic resin, and the resulting mixture is formed into a hydrogel, then extruded, to form multicomponent SAP fibers.

In yet another method, a rubbery gel of an acidic resin and a rubbery gel of a basic resin, each optionally surface crosslinked and/or annealed, are coextruded, and the coextruded product is dried, and optionally surface crosslinked and/or annealed, to form multicomponent SAP fibers containing microdomains of the acidic resin and the basic resin, as illustrated in FIGS. 3 and 4.

Another method utilizes spinning technology, wherein a first polymer, e.g., poly(vinylamine), is spun in the form of a filament, then the freshly spun filament is coated with a second polymer, e.g., poly(acrylic acid), to form (after drying) a core-sheath multicomponent SAP fiber.

Figure 5B:
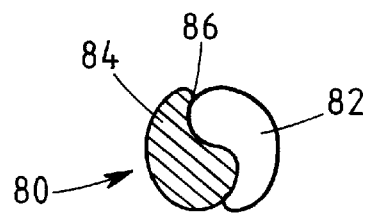

In yet another method, a filament of an acidic resin is prepared by standard spinning techniques, and a filament of a basic resin is prepared by standard spinning techniques. The two filaments then are twisted together, before and/or after optional surface crosslinking and annealing, and then dried and formed into multicomponent SAP fibers, as illustrated in FIG. 5.

The method of preparing the present multicomponent SAP fibers, therefore, typically utilizes, but does not require, a spinning or an extrusion step. Other methods of preparation wherein the multicomponent SAP fiber contains at least one microdomain of an acidic resin and at least one microdomain of a basic resin in contact or in close proximity with each other also can be used.

In embodiments wherein an acidic resin and a basic resin are present as microdomains within a matrix of a matrix resin, particles of an acidic resin and a basic resin are admixed with a rubbery gel of a matrix resin, and the resulting mixture is extruded, then dried, to form multicomponent SAP fibers having microdomains of an acidic resin and a basic resin dispersed in a continuous phase of a matrix resin. Alternatively, rubbery gels of an acidic resin, basic resin, and matrix resin can be coextruded to provide a multicomponent SAP fibers containing microdomains of an acidic resin, a basic resin, and a matrix resin. In this embodiment, the acidic resin, basic resin, and resulting multicomponent SAP fibers, each can be optionally surface crosslinked and/or annealed. Similarly, the matrix resin, acidic resin, and basic resin can be spun to form a core-sheath or twisted SAP fiber embodiment of the multicomponent SAP fibers.

The matrix resin is any resin that allows fluid transport such that a liquid medium can contact the acidic and basic resin. The matrix resin typically is a hydrophilic resin capable of absorbing water. Nonlimiting examples of matrix resins include poly(vinyl alcohol), poly(N-vinylformamide), polyethylene oxide, poly(meth)acrylamide, poly(hydroxyethyl acrylate), hydroxyethylcellulose, methylcellulose, and mixtures thereof. The matrix resin also can be a conventional water-absorbing resin, for example, a polyacrylic acid neutralized greater than 25 mole %, and typically greater than 50 mole %.

In preferred embodiments, the acidic resin, the basic resin, and/or the multicomponent SAP particles are surface treated and/or annealed. Surface treatment and/or annealing results in surface crosslinking of the particle. In especially preferred embodiments, the acidic and/or basic resins comprising the multicomponent SAP fibers are surface treated and/or annealed, and the entire multicomponent SAP fiber is surface treated and/or annealed. It has been found that surface treating and/or annealing of an acidic resin, a basic resin, and/or a multicomponent SAP fiber of the present invention enhances the ability of the resin or multicomponent SAP fiber to absorb and retain aqueous media under a load.

Surface crosslinking is achieved by contacting an acidic resin, a basic resin, and/or a multicomponent SAP fiber with a solution of a surface crosslinking agent to wet predominantly only the outer surfaces of the resin or SAP particle. Surface crosslinking and drying of the resin or multicomponent SAP particle then is performed, preferably by heating at least the wetted surfaces of the resin or multicomponent SAP fibers.

Typically, the resins and/or SAP fibers are surface treated with a solution of a surface crosslinking agent. The solution contains about 0.01% to about 4%, by weight, surface crosslinking agent, and preferably about 0.4% to about 2%, by weight, surface crosslinking agent in a suitable solvent, for example, water or an alcohol. The solution can be applied as a fine spray onto the surface of freely tumbling resin particles or multicomponent SAP particles at a ratio of about 1:0.01 to about 1:0.5 parts by weight resin or SAP particles to solution of surface crosslinking agent. The surface crosslinker is present in an amount of 0% to about 5%, by weight of the resin or SAP fiber, and preferably 0% to about 0.5% by weight. To achieve the full advantage of the present invention, the surface crosslinker is present in an amount of about 0.001% to about 0.1% by weight.

The crosslinking reaction and drying of the surface-treated resin or multicomponent SAP fibers are achieved by heating the surface-treated polymer at a suitable temperature, e.g., about 25° C. to about 150° C., and preferably about 105° C. to about 120° C. However, any other method of reacting the crosslinking agent to achieve surface crosslinking of the resin or multicomponent SAP fibers, and any other method of drying the resin or multicomponent SAP fibers, such as microwave energy, or the such as, can be used.

With respect to the basic resin, or multicomponent SAP fibers having a basic resin present on the exterior of the fibers, suitable surface crosslinking agents include di- or polyfunctional molecules capable of reacting with amino groups and crosslinking a basic resin. Preferably, the surface crosslinking agent is alcohol or water soluble and possesses sufficient reactivity with a basic resin such that crosslinking occurs in a controlled fashion at a temperature of about 25° C. to about 150° C.

Nonlimiting examples of suitable surface crosslinking agents for basic resins include:

(a) dihalides and disulfonate esters, for example, compounds of the formula

wherein p is a number from 2 to 12, and Y, independently, is halo (preferably bromo), tosylate, mesylate, or other alkyl or aryl sulfonate esters;

(b) multifunctional aziridines;

(c) multifunctional aldehydes, for example, glutaraldehyde, trioxane, paraformaldehyde, terephthaldehyde, malonaldehyde, and glyoxal, and acetals and bisulfites thereof;

(d) halohydrins, such as epichlorohydrin;

(e) multifunctional epoxy compounds, for example, ethylene glycol diglycidyl ether, bisphenol A diglycidyl ether, and bisphenol F diglycidyl ether, (f) multifunctional carboxylic acids and esters, acid chlorides, and anhydrides derived therefrom, for example, di- and polycarboxylic acids containing 2 to 12 carbon atoms, and the methyl and ethyl esters, acid chlorides, and anhydrides derived therefrom, such as oxalic acid, adipic acid, succinic acid, dodecanoic acid, malonic acid, and glutaric acid, and esters, anhydrides, and acid chlorides derived therefrom;

(g) organic titanates, such as TYZOR AA, available from E.I. DuPont de Nemours, Wilmington, Del.;

(h) melamine resins, such as the CYMEL resins available from Cytec Industries, Wayne, N.J.;

(i) hydroxymethyl ureas, such as N,N'-dihydroxymethyl-4,5-dihydroxyethylene urea;

(j) multifunctional isocyanates, such as toluene diisocyanate, isophorone diisocyanate, methylene diisocyanate, xylene diisocyanate, and hexamethylene diisocyanate; and (k) other crosslinking agents for basic water-absorbing resins known to persons skilled in the art.

A preferred surface crosslinking agent is a dihaloalkane, ethylene glycol diglycidyl ether (EGDGE), or a mixture thereof, which crosslink a basic resin at a temperature of about 25° C. to about 150° C. Especially preferred surface crosslinking agents are dibromoalkanes containing 3 to 10 carbon atoms and EGDGE.

With respect to the acidic water-absorbing resins, or multicomponent SAP particles having an acidic resin on the exterior of the fibers, suitable surface crosslinking agents are capable of reacting with acid moieties and crosslinking the acidic resin. Preferably, the surface crosslinking agent is alcohol soluble or water soluble, and possesses sufficient reactivity with an acidic resin such that crosslinking occurs in a controlled fashion, preferably at a temperature of about 25° C. to about 150° C.

Nonlimiting examples of suitable surface crosslinking agents for acidic resins include:

(a) polyhydroxy compounds, such as glycols and glycerol;

(b) metal salts;

(c) quaternary ammonium compounds;

(d) a multifunctional epoxy compound;

(e) an alkylene carbonate, such as ethylene carbonate or propylene carbonate;

(f) a polyaziridine, such as 2,2-bishydroxymethyl butanol tris[3-(1-aziridine propionate]);

(g) a haloepoxy, such as epichlorhydrin;

(h) a polyamine, such as ethylenediamine;

(i) a polyisocyanate, such as 2,4-toluene diisocyanate; and (j) other crosslinking agents for acidic water-absorbing resins known to persons skilled in the art.

Figure 6:
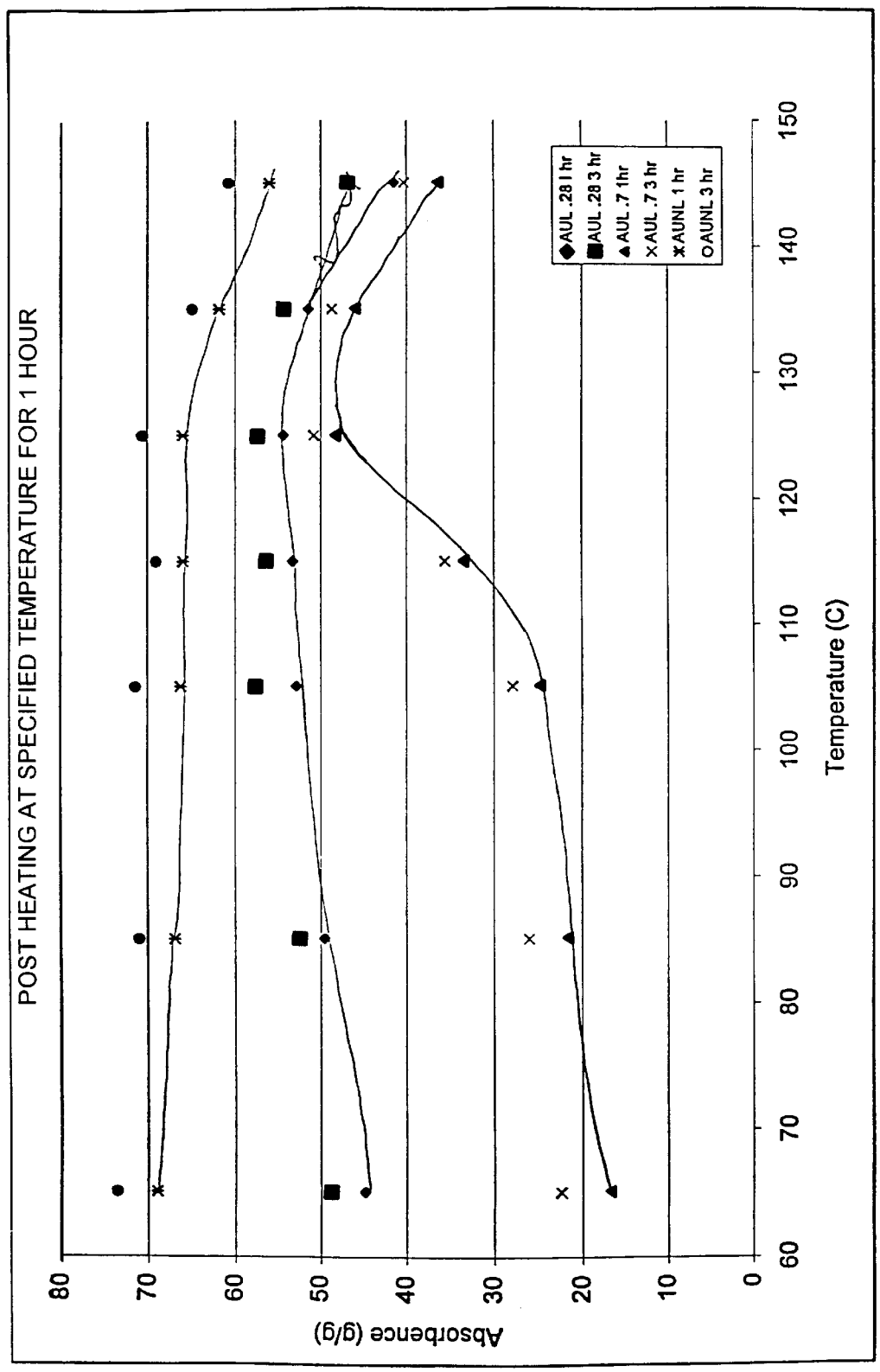
FIG. 6 contains plots of absorbance (in grams of synthetic urine per gram of multicomponent SAP granules) vs. annealing temperature for a one-hour annealing step.
Figure 7:
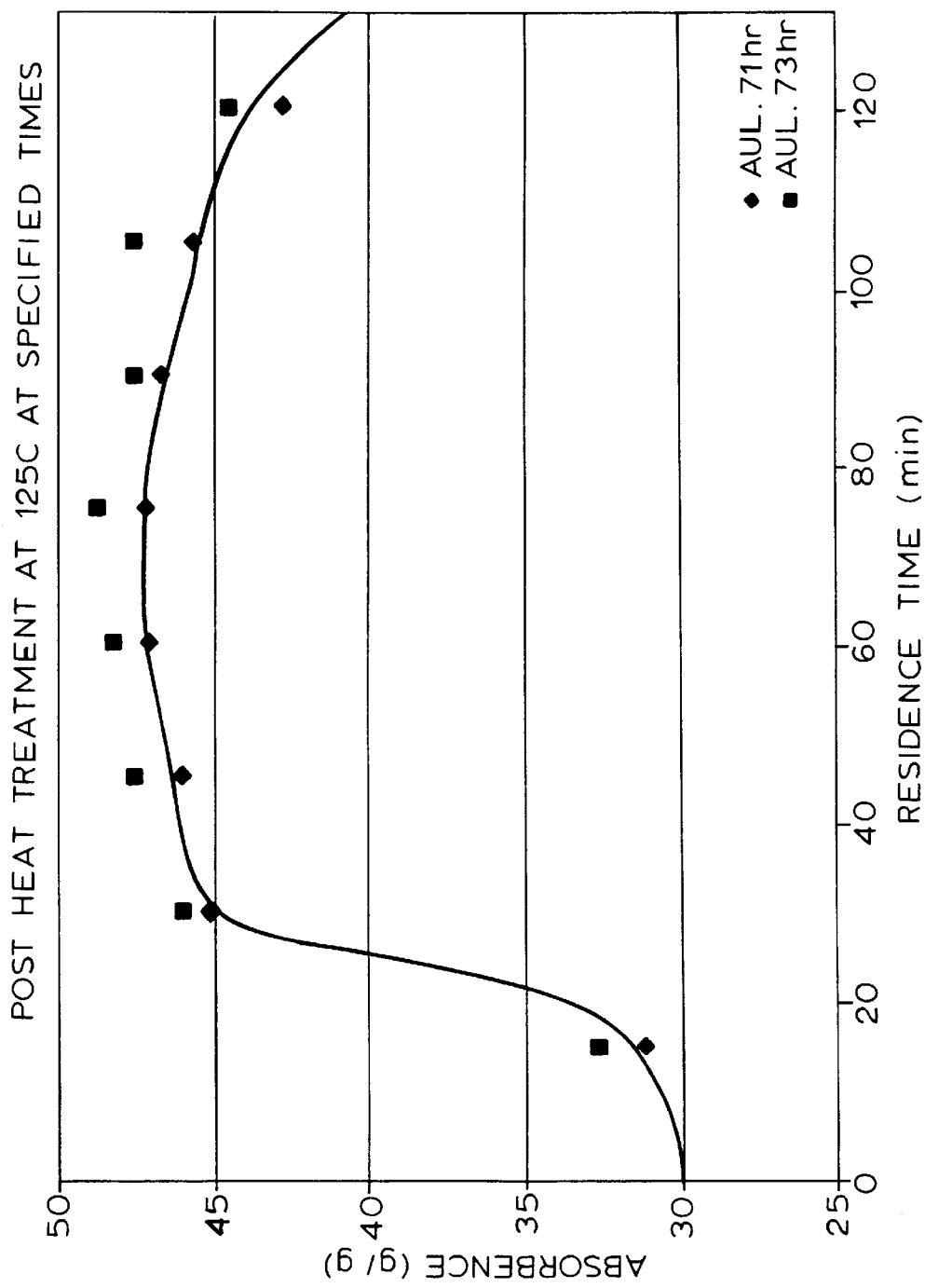
FIG. 7 contains a plot of absorbance (in grams of synthetic urine per gram of multicomponent SAP granules) vs. time for an annealing step performed at 125° C.

In addition to, or in lieu of, surface treating, the acidic resin, the basic resin, the matrix resin, the entire SAP fiber, or any combination thereof can be annealed to improve water absorption and retention properties under a load. It has been found that heating a resin for a sufficient time at a sufficient temperature above the Tg (glass transition temperature) of the resin or microdomains improves the absorption properties of the resin. FIGS. 6 and 7 contain graphs showing the effect of annealing time and temperature on the absorption properties of multicomponent SAP granules comprising 55% by weight poly(vinylamine) and 45% by weight poly(acrylic acid). Typically, a multicomponent SAP fiber of the present invention is subjected to a sufficient temperature for a sufficient time to heat and anneal the external and the internal portions of the fiber.

The graphs in FIGS. 6 and 7 show that heating a multicomponent SAP granule for about 20 to about 120 minutes at a temperature of about 60° C. to about 150° C. improves absorption properties. The absorption properties, i.e., AUL and AUNL, graphed in FIGS. 6 and 7 are discussed in detail hereafter. Preferably, annealing is performed for about 30 to about 100 minutes at about 80° C. to about 140° C. To achieve the full advantage of annealing, the SAP fibers are annealed for about 40 to about 90 minutes at about 100° C. to about 140° C.

In accordance with an important feature of the present invention, a strong acidic resin can be used with either a strong basic resin or a weak basic resin, or a mixture thereof. A weak acidic resin can be used with a strong basic resin or a weak basic resin, or a mixture thereof. Preferably, the acidic resin is a weak acidic resin and the basic resin is a weak basic resin. This result is unexpected in view of the ion exchange art wherein a combination of a weak acidic resin and a weak basic resin does not perform as well as other combinations, e.g., a strong acidic resin and a strong basic resin. In more preferred embodiments, the weak acidic resin, the weak basic resin, and/or the multicomponent SAP fibers are surface crosslinked and/or annealed.

As previously discussed, sodium poly(acrylate) conventionally is considered the best SAP, and, therefore, is the most widely used SAP in commercial applications. Sodium poly(acrylate) has polyelectrolytic properties that are responsible for its superior performance in absorbent applications. These properties include a high charge density, and charge relatively close to the polymer backbone.

However, an acidic resin in the free acid form, or a basic resin in the free base form, typically do not function as a commercially useful SAP because there is no ionic charge on either type of polymer. A poly(acrylic acid) resin, or a poly(vinylamine) resin, are neutral polymers, and, accordingly, do not possess the polyelectrolytic properties necessary to provide SAPs useful commercially in diapers, catamenial devices, and similar absorbent articles. The driving force for water absorption and retention, therefore, is lacking. This is illustrated in Tables 3 and 4 showing the relatively poor absorption and retention properties for a neutral poly(DAEA) in absorbing synthetic urine. However, when converted to a salt, an acidic resin, such as a polyacrylic acid, or a basic resin, such as a poly(dialkylaminoalkyl (meth)acrylamide), then behave such as a commercially useful SAP.

It has been found that basic resins, in their free base form, are useful components in superabsorbent materials further containing an acidic water-absorbing resin. For example, a superabsorbent material comprising an admixture of a poly(dialkylaminoalkyl (meth)acrylamide) and an acidic water-absorbing resin, such as polyacrylic acid, demonstrates good water absorption and retention properties. Such an SAP material comprises two uncharged, slightly crosslinked polymers, each of which is capable of swelling and absorbing aqueous media. When contacted with water or an aqueous electrolyte-containing medium, the two uncharged polymers neutralize each other to form a superabsorbent material. This also reduces the electrolyte content of the medium absorbed by polymer, further enhancing the polyelectrolyte effect. Neither polymer in its uncharged form behaves as an SAP by itself when contacted with water. However, superabsorbent materials, which contain a simple mixture of two resins, one acidic and one basic, are capable of acting as an absorbent material because the two resins are converted to their polyelectrolyte form. These superabsorbent materials have demonstrated good water absorption and retention properties.

In the present multicomponent SAP fibers, the weak basic resin is present in its free base, e.g., amine, form, and the acidic resin is present in its free acid form. It is envisioned that a low percentage, i.e., about 25% or less, of the amine and/or acid functionalities can be in their charged form. The low percentage of charged functionalities does not adversely affect performance of the SAP fibers, and can assist in the initial absorption of a liquid. A strong basic resin is present in the hydroxide or bicarbonate, i.e., charged, form.

The present multicomponent SAP fibers are useful in articles designed to absorb large amounts of liquids, especially electrolyte-containing liquids, such as in diapers and catamenial devices.

The following nonlimiting examples illustrate the preparation of the multicomponent SAP fibers of the present invention. In the test results set forth herein, the multicomponent SAP particles of the present invention were tested for absorption under no load (AUNL) and absorption under load at 0.28 psi and 0.7 psi (AUL (0.28 psi) and AUL (0.7 psi)). Absorption under load (AUL) is a measure of the ability of an SAP to absorb fluid under an applied pressure. The AUL was determined by the following method, as disclosed in U.S. Pat. No. 5,149,335, incorporated herein by reference.

An SAP (0.160 g +/−0.001 g) is carefully scattered onto a 140-micron, water-permeable mesh attached to the base of a hollow Plexiglas cylinder with an internal diameter of 25 mm. The sample is covered with a 100 g cover plate and the cylinder assembly weighed. This gives an applied pressure of 20 g/cm$^2$ (0.28 psi). Alternatively, the sample can be covered with a 250 g cover plate to give an applied pressure of 51 g/cm$^2$ (0.7 psi). The screened base of the cylinder is placed in a 100 mm petri dish containing 25 milliliters of a test solution (usually 0.9% saline), and the polymer is allowed to absorb for 1 hour (or 3 hours). By reweighing the cylinder assembly, the AUL (at a given pressure) is calculated by dividing the weight of liquid absorbed by the dry weight of polymer before liquid contact.

EXAMPLE 1

Preparation of Poly(acrylic acid) Particles 0% Neutralized (Poly(AA) DN=0)

A monomer mixture containing acrylic acid (270 grams), deionized water (810 grams), methylenebisacrylamide (0.4 grams), sodium persulfate (0.547 grams), and 2-hydroxy-2-methyl-1-phenyl-propan-1-one (0.157 grams) was prepared, then sparged with nitrogen for 15 minutes. The monomer mixture was placed into a shallow glass dish, then the monomer mixture was polymerized at an initiation temperature of 10° C. under 20 mW/cm$^2$ of UV light for about 12 to about 15 minutes. The resulting poly(AA) was a rubbery gel.

The rubbery poly(AA) gel was cut into small pieces, then extruded three times through a Kitchen-Aid Model K5SS mixer with meat grinder attachment. During extrusion, sodium metabisulfite was added to gel to react with unreacted monomer. The extruded gel was dried in a forced-air oven at 145° C. for 90 minutes, and finally ground and sized through sieves to obtain the desired particle size of about 180 to about 710 μm (microns).

This procedure provided a lightly crosslinked polyacrylic acid with a degree of neutralization of zero (DN=0). The polyacrylic acid (DN=0) absorbed 119.5 g of 0.1 M sodium hydroxide (NaOH) per gram of polymer and 9.03 g synthetic urine per gram of polymer under a load of 0.7 psi.

EXAMPLE 2

Preparation of a Crosslinked Poly(vinylamine) Resin Particles

To 100 g of an 8% by weight aqueous poly(vinylamine) solution was added about 2 mol % (0.66 g) of ethylene glycol diglycidyl ether (EGDGE). The resulting mixture was stirred for about 5 minutes to dissolve the EGDGE, then the homogeneous mixture was placed in an oven, heated to about 60° C., and held for two hours to gel. The resulting gel then was extruded three times, and dried to a constant weight at 60° C. The dried, lightly crosslinked poly(vinylamine) (poly(VAm)) then was cryogenically milled to form a granular material (about 180 to about 710 μm). The crosslinked poly(VAm) absorbed 59.12 g/g of 0.1 M hydrochloric acid under no load, and 17.3 g/g of synthetic urine under a load of 0.7 psi.

EXAMPLE 3

Preparation of Poly(acrylic acid) Fibers by Dry Spinning

Figure 8:
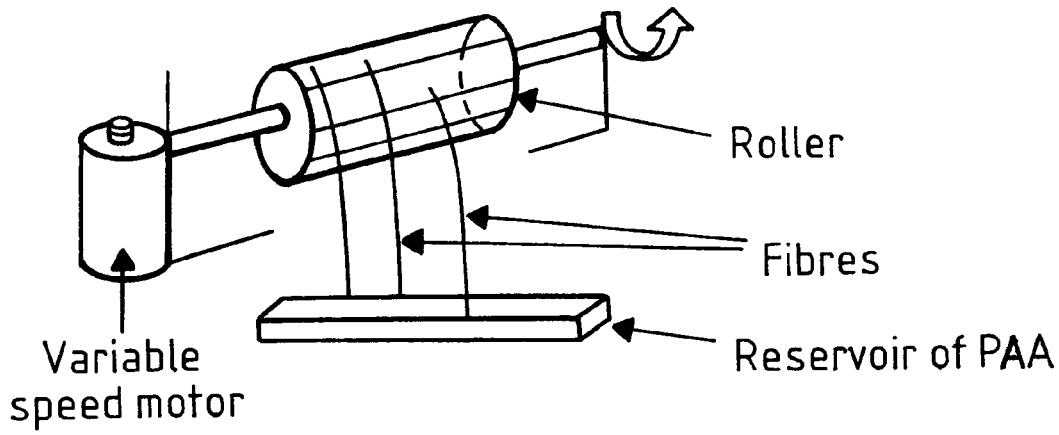
FIG. 8 is a schematic illustration of a dry spinning apparatus.

A spinning solution was prepared by concentrating an aqueous 35% (w/w) solution of uncrosslinked poly(acrylic acid) (poly(AA)), molecular weight about 250,000, to 55% (w/w). To this solution was added EGDGE (0.5% to 5% mol/mol poly(AA)) and triethylamine (5% mol/mol poly (AA)), and the resulting mixture was mixed to produce a homogeneous spinning solution. The viscosity of the spinning solution, at 55% (w/w), was 13,000 cps (by Reverse Flow Viscometer, size 8, at 25° C.). The spinning solution was placed in a Petri dish and fibers were drawn vertically upwards to a rotating drum (diameter of 15.5 cm). The dry spinning apparatus is illustrated in FIG. 8. The pull off speed was about 54 rpm with a filament draw length of 500 mm. The drawn fibers were cured either by microwave using 720 watts (W) power (2 minutes for 5% EGDGE) or by a conventional fan-assisted oven at 60° C. (60 minutes for 5% EGDGE). The time needed to cure the fiber was dependent upon the concentration of EGDGE. In the preparation of poly(AA) by dry spinning, the concentration of EGDGE in the spinning solution typically is about 0.5 to about 5% (mol/mol poly(AA)). The addition of triethylamine as a cure catalyst resulted in a faster cure, which occurred at a lower temperature.

The resulting poly(AA) fibers were about 25 μm in diameter and 0.71 denier (0.078 tex). The fibers absorbed about 69.9 g/g of 0.1 M NaOH at no load after 1 hour, and about 17.6 g/g of synthetic urine at 0.28 psi after 1 hour.

EXAMPLE 4

Preparation of Poly(vinylamine) Fibers by Wet Spinning

Figure 9:
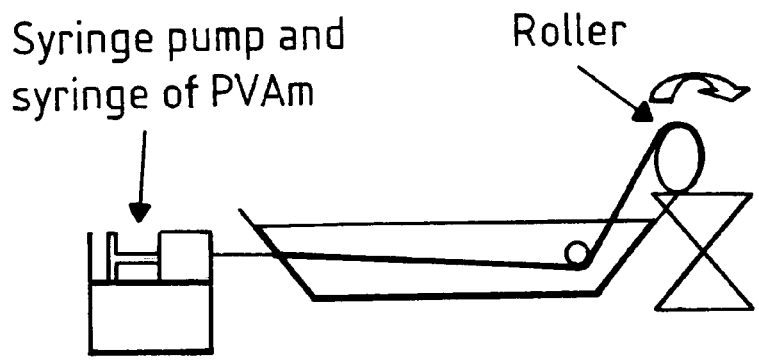
FIG. 9 is a schematic illustration of a wet spinning apparatus.

A spinning solution was prepared by concentrating a 6% w/w aqueous solution of poly(VAm) to 10% w/w poly (VAm) (molecular weight about 190,000). EGDGE (0.025 mol %) was added to the poly(VAm) solution, and mixed to provide a homogeneous solution. The solution then was heated for about 30 minutes at about 40° C., and was spinnable. The resulting spinning solution was introduced directly into a coagulation bath through a spinnerette submersed in a coagulating medium. The coagulation medium in the coagulation bath contained a mixture of EGDGE, typically 0.5% (w/w), and acetone. The concentration of EGDGE typically is about 0.5 to about 5% (w/w). The spinning solution was placed in a syringe fitted with a 23 gauge needle. The poly(VAm) was injected into the coagulating medium at a flow rate of 0.02 ml/min, and the resulting poly(VAm) was drawn off at a wind-up rate of 64 rpm. The diameter of the drum was 12 cm. The wet spinning apparatus is illustrated in FIG. 9. The poly(VAm) fibers had a diameter of 28 μm and were 5.5 denier (0.61 tex). Curing was performed in an oven at 80° C. for 30 minutes. The poly(VAm) fiber absorbed 68.3 g/g (after 1 hour) and 73.5 g/g (after 3 hours) of 0.1 M hydrochloric acid under no load, and 19.6 g/g (after 1 hour) under a load of 0.28 psi.

Poly(VAm) fibers also were produced from the identical spinning solution using a dry-jet wet spinning technique. In this technique, the spinnerette was positioned above the coagulation bath and the fiber originally was spun in air, then pulled through the coagulation bath.

As illustrated above, the physical properties of poly(AA) permit dry spinning of the polymer. Poly(AA) has a high extensional viscosity that allows stringing of the polymer solution and drawing of filaments, or fibers, from a poly (AA) spinning solution. Poly(VAm) does not have the physical properties necessary for dry spinning, and therefore is subjected to a wet spinning process. In the spinning of an acidic or a basic water-absorbing polymer, persons skilled in the art can determine whether a dry spinning or a wet spinning process should be used based on the properties of the resin.

EXAMPLE 5

Preparation of Twisted Rope Multicomponent SAP Fibers

A multicomponent SAP fiber of the present invention was prepared by twisting together a poly(AA) fiber of Example 3 and a poly(VAm) fiber of Example 4 to provide intimate contact between the acidic and basic water-absorbing resins. After twisting the acidic and basic water-absorbing fibers together, the resulting twisted rope fiber was heated in a 125° C. oven for about 10 to about 20 minutes. Twisted rope fibers containing a 50:50 mole ratio of poly(AA) of Example 3 and poly(VAm) of Example 4 absorbed aqueous media as follows:

| Aqueous Testing Medium | AUL[1] (g/g) (after 1 hr) | | AUL (g/g) (after 4 hr) | |
|---|---|---|---|---|
| Synthetic urine | 33.0[4] | (20.2)[3] | 35.7 | (26.2) |
| | 30.4 | | 36.4 | |
| 0.9% saline | 24.1 | (19.6) | 25.4 | (21.3) |
| | 23.9 | | 24.6 | |
| Synthetic blood[2] | 29.2 | (24.1) | 30.0 | (26.1) |
| | 27.2 | | 28.8 | |

[1]Absorbance under load of 0.7 psi;
[2]PLASMION ®, available from Rhone-Poulenc Rorer Bellon, Neilly sur Seine, Belgium;
[3]the value in parentheses is the amount of aqueous medium absorbed by a commercial SAP fiber, i.e., OASIS ™, available from Allied Colloids, England, and is included for comparative purposes; and
[4]absorption tests were run in duplicate.

In another example, a twisted fiber containing a 2:1 mole rate of poly(VAm) fiber to poly(AA) fiber was prepared. This twisted fiber also exhibited excelent fluid adsorption properties. In addition, during hydration of the twisted fiber, distinct entanglement of the fibers was observed.

In Example 5, the twisted rope was annealed after the fibers were twisted together. However, annealing of the individual fibers, prior to braiding, also can be performed, as well as annealing of the individual fibers followed by annealing of the twisted rope fiber.

Although Example 5 is directed to a single fiber of a poly(AA) and a single fiber of a poly(VAm) twisted together in the form of a braid, a twisted rope fiber of the present invention also encompasses embodiments wherein one or more poly(AA) fibers and one or more poly(VAm) fibers are twisted together in the form of a braid. Accordingly, embodiments wherein one or a plurality of (e.g., 1 to 500) poly(AA) fibers twisted together with one or a plurality of (e.g., 1 to 500) poly(VAm) fibers also are within the scope of the present invention.

In the twisted fiber embodiment, the mole ratio of basic resin to acidic resin is about 5:1 to about 1:5, and preferably about 3:1 to about 1:3. To achieve the full advantage of the present invention, the mole ratio is about 2:1 to about 1:2.

The effect of cure time and cure temperature on absorbency of a 50:50 mole ratio twisted fiber of Example 5 also was examined. The results of this test are summarized in Table 1.

TABLE 1

Effect of cure time and temperature on the absorbency of twisted fibers

| Time of cure (mins) | Temp of cure (° C.) | AUL[1] (g/g) (after 1 hr) | AUL[1] (g/g) (after 3 hr) |
|---|---|---|---|
| 30 | 80 | 33.08 | 37.66 |
| 10 | 125 | 38.41 | 40.03 |
| 20 | 125 | 55.46 | 63.21 |
| 30 | 125 | 33.53 | 36.80 |
| 120 | 125 | 29.28 | 32.11 |

[1]amount of synthetic urine absorbed under a load of 0.7 psi.

Figure 10:
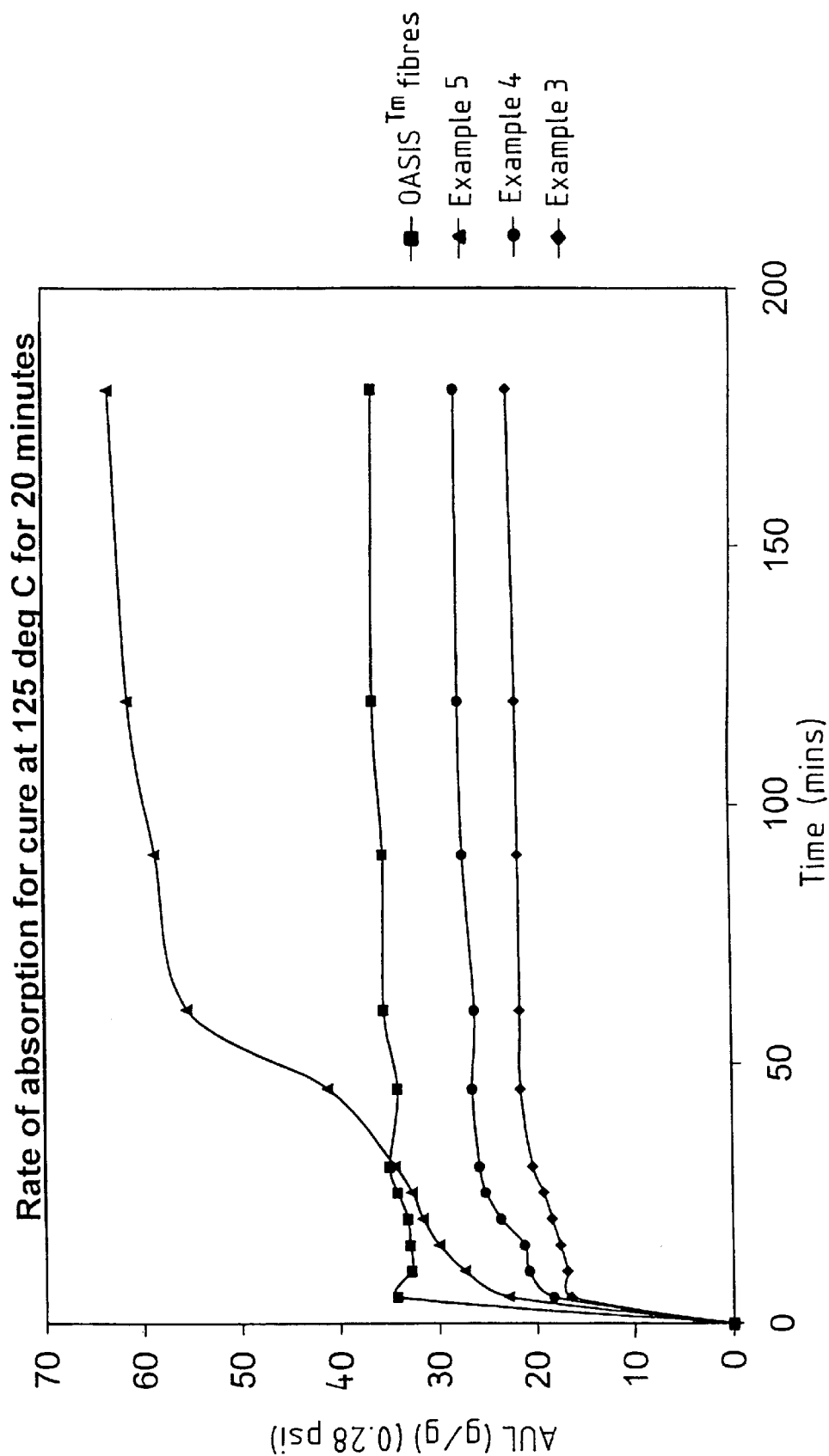
FIG. 10 contains plots of AUL (0.28 psi) (g/g) vs. time for rate of absorption of twisted SAP fibers cured at 125° C. for 20 mins.

The rate of absorption for the 50:50 mole ratio twisted fibers of Example 5, cured at 125° C. for 20 minutes, was compared to OASIS™ fibers, poly(VAm) fibers of Example 4, and poly(AA) fibers of Example 3. The results are summarized in FIG. 10. FIG. 10 shows that the twisted SAP fibers absorb more rapidly than poly(VAm) and poly(AA) fibers, and over time outperforms OASIS™ fibers.

A test also was performed to determine whether fiber length affected absorption The twisted fiber multicomponent SAP of Example 5, having a length of 5, 10, 20, and 40 mm, was compared to poly(AA) granules, OASIS™ fibers, and physical blends of poly(AA) and poly(VAm) fibers having a length 5, 10, 20, and 40 mm in length, for absorption rate of synthetic urine under 0.28 psi pressure. Absorption improved with increasing fiber length up to 20 mm, then decreased at 40 mm. The twisted fiber multicomponent SAP outperformed the blend of poly(AA) and poly(VAm) fibers.

A multicomponent SAP fiber of the present invention also can be in the form of a core of a first resin and a sheath, or shell, of a second resin. This embodiment is illustrated in Examples 6 and 7.

EXAMPLE 6

Preparation of Multicomponent SAP Fibers Having a Poly(AA) Core and a Poly(VAm) Sheath Poly(AA) fibers were prepared as set forth in Example 3. The poly(AA) fibers then were passed through a solution of poly(VAm) (10–20% solids like in Example 4). The resulting coated fiber then was passed through a coagulation bath containing EGDGE (0.5 w/w) and acetone. The resulting core/sheath multicomponent SAP fibers were dried and cured in a fan-assisted oven at 60° C. for 1 hour. A typical core/sheath multicomponent SAP fibers contained about 0.008 g of poly(AA) and 0.011 g of poly(VAm), or a mole ratio of acrylic acid to vinylamine of 1:2.3. The multicomponent SAP fiber of Example 6 absorbed 18.2 g/g of synthetic urine after 60 minutes under a 0–7 psi load. In comparison, the poly(AA) fibers of Example 3 absorbed 8.4 g/g under identical conditions.

EXAMPLE 7

Figure 11:
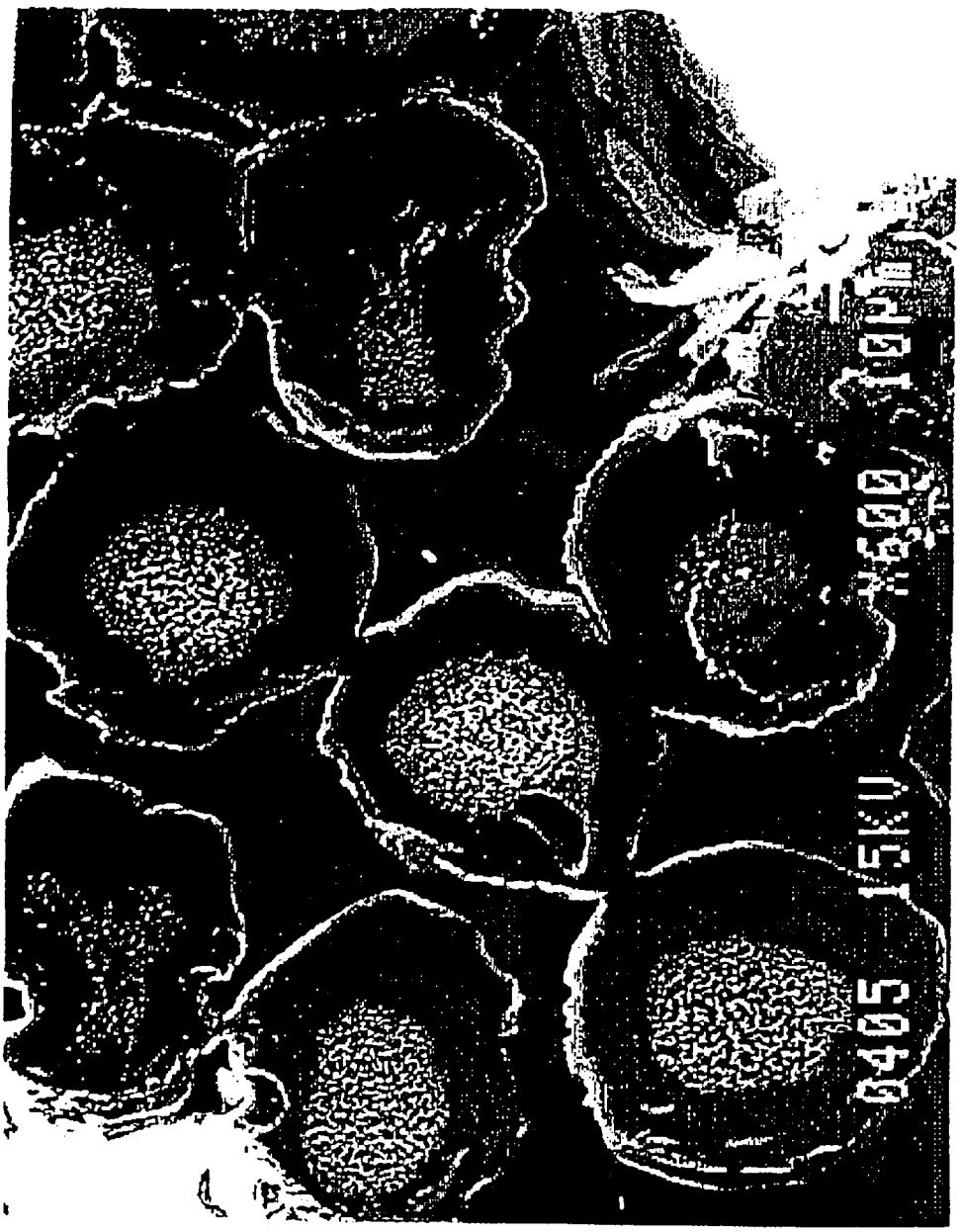
FIGS. 11 and 12 are scanning electron micrographs of the multicomponent SAP fibers of Example 7.
Figure 12:
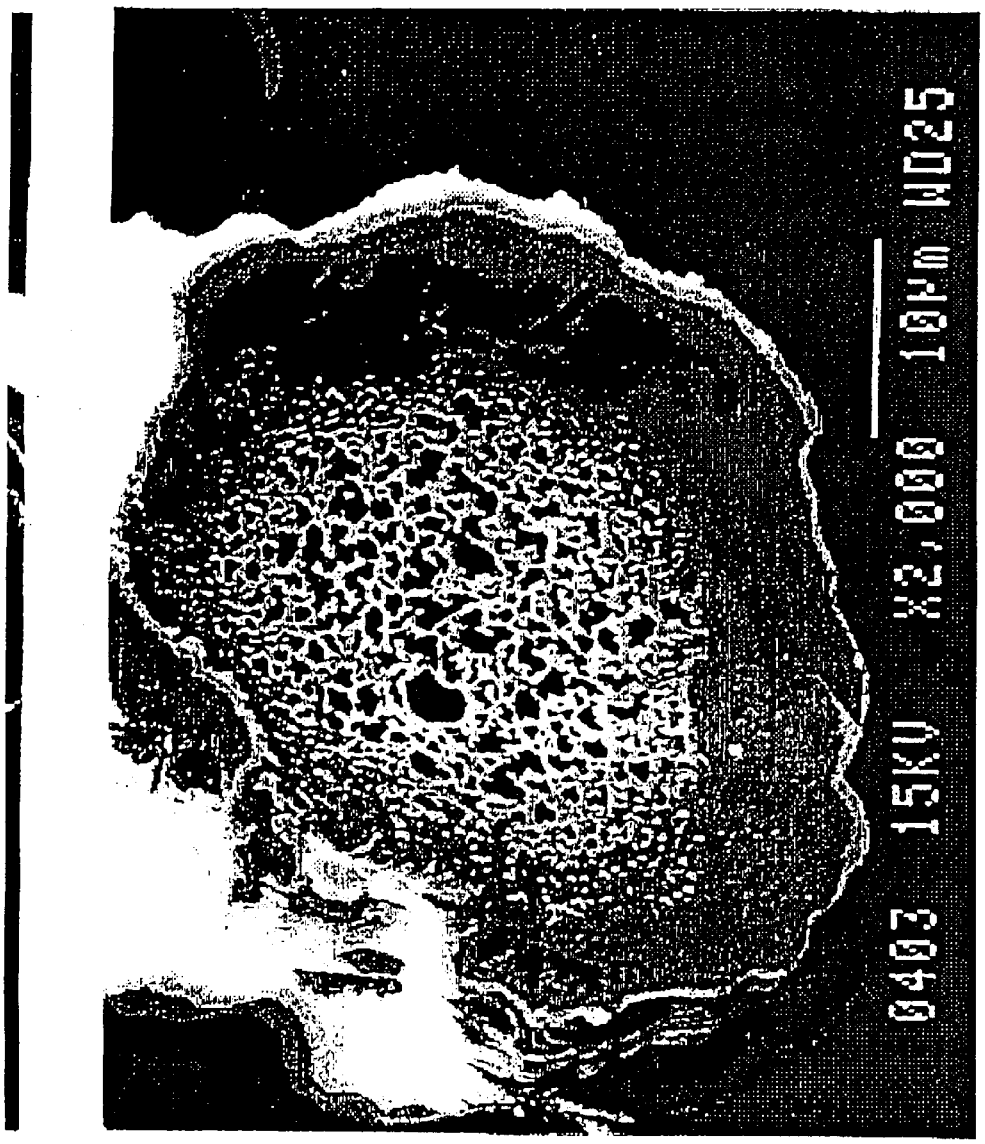

Preparation of Multicomponent SAP Fibers Having a Poly(VAm) Core and a Poly(AA) Sheath An aqueous polyvinylamine solution (10% solids) was combined with 0.025 mol % of EGDGE crosslinker. The resulting solution was mixed until homogeneous, and then allowed to crosslink lightly at 40° C. for 20 minutes to form a spinning dope. The dope was injected directly into a coagulation bath containing EGDGE, typically in an amount of about 0.25% to about 1% based on a w/w % concentration. The coagulant in the bath was a nonsolvent for poly (VAm), typically acetone. The poly(VAm) was spun directly into the bath at a flow rate of 2.54 cm$^3$/hr. The fiber was produced at a fast rate, with coagulation occurring initially from the outside. The process started with the production of a skin. This type of coagulation produced a fiber morphology having voids within the core, as illustrated in FIGS. 11–13. The fiber was drawn through the bath, and upwards from the bath. On drawing the fiber from the coagulation bath, it was passed over an acetone soaked roller and then passed into a coating bath containing poly(AA) and EGDGE. This bath contained a concentrated aqueous solution of poly(AA) (50–70 w/w %) diluted to about 15% w/w % polyacrylic acid with a polar solvent, typically acetone. The EGDGE was present at about 0.5 mol %. Passing the fiber through this bath coated the core of poly(VAm) with a sheath of poly(AA). After passing through this bath, the fiber was passed over a second acetone-coated roller and into a doping bath containing 5 wt % triethylamine in acetone. After passing the fiber through this solution, the fiber was wound at a speed of about 50–60 rpm. The fibers thus produced were removed from the roller and cured for 30 minutes at 125° C. The multicomponent SAP fibers were 25 denier (2.8 tex). Increasing the cure time of the fibers at 125° C. up to 60 minutes or longer, resulted in a change in the morphology of the hydrated fibers. The hydrated fiber gel was harder than hydrated fibers cured for only 20 to 30 minutes. Upon removal of the fibers from the AUL test cell, the structure fell apart and no longer resembled a mat.

The multicomponent SAP fibers of Example 7 were tested for an ability to absorb artificial urine, artificial blood, and 0.9% saline. The test results are summarized below.

| Aqueous Testing medium | AUL (after 1 hour @ 0.7 psi) | AUL (after 4 hour @ 0.7 psi) |
| --- | --- | --- |
| Synthetic urine | 24.9 | 26.0 |
| 0.9% saline | 19.3 | 24.4 |
| Synthetic blood | 20.5 | 22.5 |

Upon hydration, the fibers of Example 7 formed a mat-type structure. On completion of the AUL test, the mat maintained its integrity, and it was possible to remove the mat as one piece. In contrast, the twisted rope fiber of Example 5 fractured into its individual fiber components after hydration. Examination of the mat produced with the core-shell fiber of Example 7 revealed an open structure with a very fibrous appearance. No free fluid was present on the surface of the fibers. Accordingly, all of the fluid was contained within the structure of the fiber. It also was observed that as the coating of poly(AA) increased, AUL values of 50 g/g were attained.

The fibers of Example 7 were tested to determine the effect of cure time on the absorbency of the fibers under a 0.7 psi load. Four samples were prepared identically, then subjected to a cure time of 1, 3, 5, or 20 minutes, each at 125° C. The test results are summarized in Table 2, showing that an increased curing time improved the absorption of synthetic urine.

TABLE 2

| Time of cure (mins) | AUL (g/g) (after 1 hr) | AUL (g/g) (after 3 hr) |
| --- | --- | --- |
| 1 | 16.9 | 17.6 |
| 3 | 17.6 | 18.9 |
| 5 | 18.9 | 20.0 |
| 20 | 29.0 | 29.5 |

The fibers of Example 7 also were prepared using an alternate procedure wherein poly(VAm) fibers prepared in Example 4 were passed through a solution containing poly (AA), EGDGE (about 0.5 to about 5 mol %), and triethylamine (5 mol %). In different runs, the fibers were dried and cured either by microwave (720 W) for 4 minutes, or by a fan-assisted oven at 60° C. for 60 minutes. A typical core-sheath SAP fiber contained 0.16 g poly(VAm) and 0.16 g poly(AA), i.e., a mole ratio of poly(VAm) to poly(AA) of 2:1. This SAP fiber absorbed 26.8 g/g of synthetic urine under a load of 0.7 psi after 60 minutes. Under the same conditions, poly(VAm) fibers absorbed 14.2 g/g of synthetic urine.

The following Examples 8–11 illustrate other embodiments of the present invention, in particular, embodiments wherein the fiber comprises microdomains of an acidic resin in a continuous phase of a basic resin, or vice versa.

EXAMPLE 8

Preparation of a Poly(VAm) Fiber Containing Microdomains of Poly(AA)

To a poly(VAm) spinning solution prepared as set forth in Example 4 was added finely milled poly(AA) fines (<20 μm diameter). The mixture was stirred until a homogeneous solution was obtained (about 5 minutes). The spinning solution was spun into an EGDGE (about 0.5% to about 5% w/w)-acetone coagulation bath as in Example 4. The resulting fibers were cured in an oven at 60° C. for 60 minutes.

A typical multicomponent SAP fiber of Example 8 contained 5.54 g of poly(VAm) and 0.11 g of poly(AA), which is a mole ratio of poly(VAm) of poly(AA) of 6:1, and 2% w/w amount of EGDGE crosslinker. These fibers absorbed 24.2 g/g synthetic urine after 1 hour under a load of 0.7 psi. An identical poly(VAm) fiber that is free of poly(AA) fines, absorbed 12.1 g/g, under identical conditions.

EXAMPLE 9

Preparation of a Poly(AA) Fiber Containing Microdomains of Poly(VAm)

To an aqueous poly(AA) solution prepared as set forth in Example 3 was added finely milled poly(VAm) fines (<20 μm diameter). The mixture was stirred until a homogeneous solution was obtained (about 5 minutes). The spinning solution was dry spun as described in Example 3. The resulting fibers were cured in an oven at 60° C. for 60 minutes.

A typical multicomponent SAP fiber of Example 9 contained 0.13 g of poly(VAm) and 4.94 g of poly(AA), which is a mole ratio of poly(VAm) to poly(AA) of 1:12, and 0.5% w/w of EGDGE crosslinker. The fibers of Example 9 absorbed 18.4 g/g of synthetic urine after 1 hour under a load of 0.7 psi. An identical poly(AA) fiber that is free of poly(VAm) fines absorbed 8.4 g/g, under identical conditions.

EXAMPLE 10

In a method identical to Example 9, VISCOMER™ was added to a solution of poly(VAm). VISCOMER™ is a commercially available poly(AA) from Chemdal Corporation, Palatine, Ill. VISCOMER™ has a molecular weight of about 4 million, and a particle size of less than 10 $\mu$m in diameter. The resulting spinning solution was spun into an EGDGE (from about 0.5 to about 5% w/w)-acetone coagulation bath as previously described. The resulting fibers were cured in an oven at 60° C. overnight.

A typical multicomponent SAP fiber of Example 10 contained a mole ratio of poly(VAm) to poly(AA) of 1:1, and 0.5% w/w of EGDGE crosslinker. The fibers of Example 10 absorbed 14.47 g/g of synthetic urine under a load 0.7 psi after 60 minutes.

EXAMPLE 11

In a method identical to Example 9, CARBOPOL™ was added to a solution of poly(VAm). CARBOPOL™ is a commercially available poly(AA) from BF Goodrich Co., Cleveland, Ohio. CARBOPOL™ has a molecular weight of about 400,000 to about 4,000,000, and a particle size of about 2 to about 7 $\mu$m in diameter. The resulting spinning solution was spun into an EGDGE (about 0.5 to about 5% w/w)-acetone coagulation bath as previously described. The resulting fibers were cured in an oven at 60° C. overnight.

A typical multicomponent SAP particle of Example 10 contained a 1:1 mole ratio of poly(VAm) to poly(AA), and 0.5% w/w of EGDGE crosslinker. The fibers of Example 11 absorbed 17.5 g/g of synthetic urine under a load of 0.7 psi after 60 minutes.

The following Example 12 illustrates an embodiment wherein poly(VAm) and poly(AA) fibers are coextruded.

EXAMPLE 12

Preparation of Multicomponent SAP Fibers by Coextrusion

Poly(VAm) fibers were prepared by the wet spinning method disclosed in Example 4. In parallel, poly(AA) fibers were prepared by the dry spinning method disclosed in Example 3. The poly(AA) fibers were passed through a heated chamber at 60° C., followed by coextrusion with the poly(VAm) fibers. The coextruded SAP fibers were cured at 60° C. for 1 hour.

A typical coextruded multicomponent SAP fiber of the present invention contains a 1:1 mole ratio of poly(VAm) to poly(AA). The coextruded fiber absorbed 28.1 g/g of synthetic urine under a load of 0.7 psi after 60 minutes. In comparison, the poly(AA) fibers of Example 3 absorbed 8.4 g/g and the poly(VAm) fibers of Example 4 absorbed 12.9 g/g under identical conditions.

The following Example 13 illustrates surface treating a multicomponent SAP fiber of the present invention.

EXAMPLE 13

Surface Treating of Multicomponent SAP Fibers

The twisted rope SAP fibers of Example 5 were passed through a solution of propylene glycol and water (80:20 w/w) to coat the twisted fibers. The coated twisted fibers then were dried in a 125° C. oven for 1 hour. The resulting surface crosslinked SAP fibers had a mole ratio of poly(AA) to poly(VAm) of 1:1, and a weight ratio of twisted fibers to surface coating of 4.7:1. The surface crosslinked multicomponent SAP fibers absorbed 10.5 g/g of synthetic urine under a load of 0.7 psi after 60 minutes.

The following tables contain absorption and retention data for the multicomponent SAP fibers of the present invention, for individual polymers present in the multicomponent SAP fibers, and for simple admixtures of the dry resins present in the multicomponent SAP fibers. The data shows a significant improvement in water absorption and retention for the present multicomponent SAP fibers containing microdomains of an acidic and/or basic resin polymers within each particle compared to the individual resins and a simple admixture of the individual resins. The data in Tables 3–8 shows the improved ability of multicomponent SAP fibers of the present invention to absorb and retain an aqueous 0.9% saline solution.

TABLE 3

| SAP | AUL (0.28 psi, 1 hr.) | AUL (0.7 psi, 1 hr.) | AUNL (1 hr.) | AUL (0.28 psi, 3 hr.) | AUL (0.7 psi, 3 hr.) | AUNL (3 hr.) |
|---|---|---|---|---|---|---|
| Poly(DAEA) alone[1] | 9.6 | 8.1 | 23.9 | 13.5 | 9.3 | 24.2 |
| Polyacrylic Acid alone[2] | 11.9 | 10.8 | 14.3 | 12.0 | 10.8 | 14.3 |
| SAP-1[3] | 11.0 | 10.9 | 45.2 | 14.8 | 14.4 | 48.0 |
| SAP-2[4] | 12.5 | 9.6 | 26.7 | 18.9 | 13.1 | 30.1 |
| SAP-3[5] | 12.4 | 11.3 | 37.3 | 16.5 | 14.7 | 42.3 |
| SAP-4[6] | 20.1 | 17.2 | 28.6 | 24.7 | 20.7 | 34.1 |
| SAP-5[7] | 25.3 | 18.2 | 35.3 | 28.1 | 23 | 38.7 |
| Multicomponent SAP-1[8] | | | | | | |
| 0[9] | 23.7 | 16.3 | 41.6 | 26.9 | 20 | 41.7 |
| 200 | 26.7 | 24.7 | 41.2 | 27.1 | 25.1 | 39.9 |
| 400 | 27.3 | 24.1 | 43.4 | 27.5 | 24.5 | 44.0 |
| 600 | 29.2 | 23.8 | 41.8 | 29.5 | 24.0 | 41.2 |
| 800 | 26.6 | 24.1 | 40.9 | 26.7 | 24.2 | 41.7 |
| 1,000 | 27.5 | 24.3 | 39.9 | 27.8 | 24.2 | 40.7 |
| Multicomponent SAP-2[10] | | | | | | |
| 0[9] | 26.3 | 15.4 | 40 | 26.9 | 17.3 | 39.4 |
| 400 | 26.5 | 20.5 | 39.3 | 27 | 22.4 | 40.3 |
| 600 | 27 | 18.3 | 40.2 | 27.1 | 20.7 | 40.6 |

[1]particle size--180–710 $\mu$m;
[2]0% neutralization, particle size--180–710 $\mu$m, surface crosslinked--600 ppm EGDGE;
[3]mixture of 60% poly(DAEA), particle sizes less than 180 nm, and 40% polyacrylic acid --0% neutralized;
[4]mixture of 60% poly(DAEA), particle sizes less than 180 nm, and 40% polyacrylic acid --0% neutralized, crosslinked with 600 ppm EGDGE;
[5]mixture of 60% poly(DAEA), particle size--180–710 $\mu$m, and 40% polyacrylic acid --0% neutralized;
[6]mixture of 60% poly(DAEA), particle size--180–710 $\mu$m, and 40% polyacrylic acid --0% neutralized, crosslinked with 600 ppm EGDGE;
[7]mixture of 60% poly(DAEA), particle sizes less than 180 $\mu$m, and 40% polyacrylic acid--20% neutralized, particle size 180–710 $\mu$m;
[8]multicomponent SAP containing microdomains of poly(DAEA) (<180 $\mu$m) as dispersed phase in poly(AA) (DN = 0) continuous phase, poly (DAEA)/poly(AA) weight ratio--60/40;
[9]ppm surface crosslinking with EGDGE; and
[10]multicomponent SAP containing microdomains of poly(DAEA) (<180 $\mu$m) as dispersed phase in poly(AA) (DN = 20) continuous phase, poly (DAEA)/poly(AA) weight ratio--60/40.

TABLE 4

| SAP | AUL (0.28 psi, 1 hr.) | AUL (0.7 psi, 1 hr.) | AUNL (1 hr.) | AUL (0.28 psi, 3 hr.) | AUL (0.7 psi, 3 hr.) | AUNL (3 hr.) |
|---|---|---|---|---|---|---|
| Poly(DMAPMA)[11] | 10.2 | 8.6 | 18 | 11.4 | 10 | 18.3 |
| Poly(DMAPMA)[12] | 9.3 | 5.2 | 17.4 | 11 | 6.9 | 17.8 |
| Polyacrylic acid[13] | 11.9 | 10.8 | 14.3 | 12.0 | 10.8 | 14.3 |
| SAP-6[14] | 14.5 | 10.9 | 18.8 | 17.2 | 14.3 | 20.9 |
| SAP-7[15] | 14 | 12 | 38.7 | 17.9 | 15.7 | 43.6 |
| SAP-8[16] | 12.5 | 10.4 | 24.8 | 14.5 | 12.4 | 24.8 |
| Multicomponent SAP-3[17] | | | | | | |
| 0[9] | 28.8 | 15 | 41.6 | 31 | 17.5 | 41.5 |
| 100 | 27.4 | 24.2 | 38.8 | 27.1 | 23.6 | 38.8 |
| 200 | 27.3 | 24.2 | 39.8 | 25.8 | 23 | 39 |
| 400 | 26 | 23 | 37 | 25.2 | 22.5 | 36.4 |
| 600 | 25.1 | 22.3 | 37.1 | 24.7 | 21.3 | 36.1 |
| Multicomponent SAP-4[18] | | | | | | |
| 0[9] | 31.9 | 11.6 | 44.2 | 31.8 | 15.7 | 44.9 |
| 200 | 27.6 | 24.3 | 37.8 | 27.5 | 23.4 | 38.1 |
| 400 | 27.5 | 23.7 | 37.4 | 27.2 | 23.1 | 38.8 |
| Multicomponent SAP-5[19] | | | | | | |
| 0[20] | 23.6 | 12.9 | 37.9 | 25 | 14.4 | 38.5 |
| 1500 | 24.7 | 16.9 | 36.4 | 25.5 | 18.3 | 37.5 |

[11]Poly(DMAPMA), particle size less than 106 μm;
[12]Poly(DMAPMA), particle size 106–180 μm;
[13]Polyacrylic acid, particle size 180–710 μm--0% neutralized, surface crosslinked with 600 ppm EGDGE;
[14]mixture of 60% Poly(DMAPMA), particle size 106–180 μm, and 40% polyacrylic acid--0% neutralized;
[15]mixture of 60% Poly(DMAPMA), particle size <106 μm, and 40% polyacrylic acid--0% neutralized;
[16]mixture of 50% Poly(DMAPMA), and 50% polyacrylic acid--0% neutralized;
[17]multicomponent SAP containing microdomains of poly(DMAPMA) (<106 μm) as dispersed phase in poly(AA) (DN = 0) continuous phase, poly(DMAPMA)/poly(AA) weight ratio 60/40;
[18]multicomponent SAP containing microdomains of poly(DMAPMA) (106–180 μm) as dispersed phase in poly(AA) (DN = 0) continuous phase, poly(DMAPMA)/poly(AA) weight ratio 60/40;
[19]multicomponent SAP containing microdomains of poly(AA) (DN = 0%) (<106 μm) as dispersed phase in poly(DMAPMA) continuous phase, poly(AA)/poly(DMAPMA) weight ratio 50/50; and
[20]ppm surface crosslinking with dibromooctane.

TABLE 5

| SAP | AUL (0.28 psi, 1 hr.) | AUL (0.7 psi, 1 hr.) | AUNL (1 hr.) | AUL (0.28 psi, 3 hr.) | AUL (0.7 psi, 3 hr.) | AUNL (3 hr.) |
|---|---|---|---|---|---|---|
| Poly(vinylamine) alone | 14.2 | 14.4 | 21.4 | 15 | 14.3 | 23.4 |
| SAP-9[21] | 21.2 | 18.6 | 28.3 | 23.8 | 20.5 | 36.3 |
| Multicomponent SAP-6[22] | | | | | | |
| 0[9] | 14.9 | 12.8 | 53.8 | 16.9 | 15.6 | 55.4 |
| 100 | 37.5 | 30.1 | 45.5 | 37.5 | 30.1 | 45.5 |
| 200 | 36.2 | 30.4 | 48.5 | 35.9 | 30.2 | 47.4 |
| 400 | 34.6 | 30.6 | 44.9 | 34.6 | 30.6 | 46.2 |

[21]mixture of 37% poly(vinylamine) and 63% poly(AA); and
[22]multicomponent SAP containing microdomains of poly(vinylamine) (<180 μm) as dispersed phase in poly(AA) (DN = 0) continuous phase, poly(vinylamine)/poly(AA) weight ratio--37/63.

TABLE 6

Coextruded Multicomponent SAP Particle
(60/40 weight ratio poly(DAEA)/poly(AA))

| Surface Treatment | AUL (0.28 psi, 1 hr.) | AUL (0.7 psi, 1 hr.) | AUNL (1 hr.) | AUL (0.28 psi, 3 hr.) | AUL (0.7 psi, 3 hr.) | AUNL (3 hr.) |
|---|---|---|---|---|---|---|
| 0 | 30.5 | 13.3 | 41.1 | 30.6 | 16.3 | 40.2 |
| 200 ppm EGDGE | 31 | 27.7 | 40.2 | 30.8 | 27.3 | 39.9 |

TABLE 7

| SAP | AUL (0.28 psi, 1 hr.) | AUL (0.7 psi, 1 hr.) | AUNL (1 hr.) | AUL (0.28 psi, 3 hr.) | AUL (0.7 psi, 3 hr.) | AUNL (3 hr.) |
|---|---|---|---|---|---|---|
| Poly(vinylguanidine) hydro-chloride alone | 21 | 16.1 | 31.2 | 22.4 | 18.0 | 32.7 |
| Multicomponent SAP-7[23] | | | | | | |
| 0[9] | 18.8 | 12.7 | 40.6 | 21.2 | 15.3 | 46.8 |
| 200 | 22 | 19.2 | 33.5 | 23.5 | 20.3 | 37.4 |

[23]multicomponent SAP containing microdomains of poly(VG) and poly(AA), with a poly(VG)/poly(AA) weight ratio--50/50.

TABLE 8

Coextruded Multicomponent SAP Particle
(37.4/62.6 weight ratio PEI/poly(AA))

| PEI Gel (% Solids) | Cross-linker Level[24] | AUL (0.28 psi, 1 hr.) | AUL (0.7 psi, 1 hr.) | AUNL (1 hr.) | AUL (0.28 psi, 3 hr.) | AUL (0.7 psi, 3 hr.) | AUNL (3 hr.) |
|---|---|---|---|---|---|---|---|
| 20 | 1.0 | 23 | 19.5 | 32 | 24.3 | 20.8 | 34.9 |
| 10 | 1.5 | 20.1 | 16.2 | 28.4 | 22.4 | 18.1 | 31.9 |

[24]mole % EGDGE.

To demonstrate that a multicomponent SAP fiber of the present invention can contain an acidic resin and/or a basic resin that is partially neutralized, a series of tests was performed on multicomponent SAP particles containing 45% by weight poly(AA) and 55% by weight polyvinylamine). The multicomponent SAP particles were prepared in an identical manner, but the percent neutralization of the poly(AA) and poly(vinylamine) was changed. The various multicomponent SAP particles were tested for an ability to absorb and retain synthetic urine, and the results are summarized in Table 9.

TABLE 9

| % Neutralized Poly(vinylamine)/ % Neutralized Poly(AA) (by weight) | Surface Crosslinking | AUL (0.7 psi, 1 hr) | AUL (0.7 psi, 3 hr) |
|---|---|---|---|
| 0/0 | None | 16.8 | 21.6 |
| 0/10 | None | 13.4 | 16.9 |
| 0/25 | None | 12.6 | 16 |
| 10/0 | None | 37.2 | 37.7 |
| 25/0 | None | 24.4 | 25.3 |
| 10/10 | None | 19.2 | 24.3 |
| 25/25 | None | 19.8 | 19.3 |
| 50/50 | None | 11.9 | 13.8 |
| 0/0 | PG/H$_2$O [1] | 43.3 | 47.6 |

TABLE 9-continued

| % Neutralized Poly(vinylamine)/ % Neutralized Poly(AA) (by weight) | Surface Crosslinking | AUL (0.7 psi, 1 hr) | AUL (0.7 psi, 3 hr) |
|---|---|---|---|
| 0/10 | PG/H$_2$O | 34 | 36.9 |
| 0/25 | PG/H$_2$O | 14.4 | 17.4 |
| 10/0 | PG/H$_2$O | 30.9 | 31.4 |
| 25/0 | PG/H$_2$O | 24.1 | 25.3 |
| 10/10 | PG/H$_2$O | 39.3 | 41.2 |
| 25/25 | PG/H$_2$O | 18.9 | 18.7 |
| 50/50 | PG/H$_2$O | 12.1 | 14.5 |

[1] Surface treatment with propylene glycol/water (80/20 ratio), dried at 125° C. for 2.5 hours.

In another series of tests, the ratio of acidic water-absorbing resin to basic water-absorbing resin in the multicomponent SAP particles was varied. In particular, Table 10 summarizes the AUNL data and the AUL data at different pressures for a series of multicomponent SAP particles containing poly(vinylamine) and poly(AA) over the range of 25% to 75% by weight. The multicomponent SAP particles used in this series of tests were multicomponent SAP particles containing 55% by weight poly(vinylamine) and 45% by weight poly[]acrylic acid). All multicomponent SAP particles used in the test were surface-crosslinked with 50 ppm EGDGE. The multicomponent SAP particles were tested for an ability to absorb and retain synthetic urine.

absorption. In practical terms, this means that acquisition of a fluid by the SAP particles, and, accordingly, the absorbent structure, such as a diaper, can be much slower than the rate at which fluids are discharged, especially in gush situations. Leakage from an absorbent structure, therefore, can occur well before the SAP particles in the absorbent structure are fully saturated, or before the fluid can diffuse or wick past the "gel blocked" particles into the remainder of the absorbent structure. Gel blocking can be a particularly acute problem if the SAP particles lack adequate gel strength, and deform or spread under stress after the SAP particles swell with absorbed fluid.

Accordingly, an SAP particle can have a satisfactory AUL value, but will have inadequate permeability or flow conductivity to be useful at high concentrations in absorbent structures. In order to have a high AUL value, it is only necessary that the hydrogel formed from the SAP particles has a minimal permeability such that, under a confining pressure of 0.3 psi, gel blocking does not occur to any significant degree. The degree of permeability needed to simply avoid gel blocking is much less than the permeability needed to provide good fluid transport properties. Accordingly, SAPs that avoid gel blocking and have a satisfactory AUL value can still be greatly deficient in these other fluid handling properties.

Accordingly, an important characteristic of the multicomponent SAP fibers of the present invention is permeability when swollen with a liquid to form a hydrogel zone or layer, as defined by the Saline Flow Conductivity (SFC) value of

TABLE 10

| Weight Ratio Poly(vinyl amine)/- Poly(AA) | AUL 0.28 psi (1 hr) | AUL 0.7 psi (1 hr) | AUL 1.4 psi (1 hr) | AUNL (1 hr) | AUL 0.28 psi (3 hr) | AUL 0.7 psi (3 hr) | AUL 1.4 psi (3 hr) | AUNL (3 hr) | AUL 0.28 psi (17 hr) | AUL 0.7 psi (17 hr) | AUL 1.4 psi (17 hr) | AUNL (17 hr) |
|---|---|---|---|---|---|---|---|---|---|---|---|---|
| 25/75 | 41.3 | 36.6 |  | 53.6 | 41.2 | 36.6 |  | 54 | 39.1 | 33.3 |  | 52.3 |
| 30/70 | 46.3 | 42.2 |  | 58.7 | 46.4 | 42.8 |  | 59.6 | 43.1 | 38.7 |  | 58.4 |
| 35/65 | 43.6 | 38.5 |  | 54.4 | 44.2 | 39.5 |  | 54.8 | 42 | 35.8 |  | 54.3 |
| 40/60 | 52.1 | 44.3 |  | 63.9 | 53.7 | 46.5 |  | 66.7 | 51.7 | 43.2 |  | 65.2 |
| 45/55 | 50.4 | 46 |  | 61.1 | 51.4 | 47.4 |  | 63.2 | 47.3 | 41.9 |  | 61.9 |
| 50/50 | 52.2 | 45 | 26 | 62.5 | 54.8 | 47.7 | 29 | 66.7 | 52.8 | 45.4 | 30.9 | 66.4 |
| 55/45 | 52.1 | 47.3 | 27.4 | 62.5 | 54.8 | 49.3 | 31.3 | 66.2 | 53.1 | 44.8 | 32.5 | 65.4 |
| 60/40 | 52.8 | 47 | 27.8 | 64.6 | 55.2 | 49.6 | 30.9 | 68 | 52.6 | 44 | 33 | 67.6 |
| 65/35 | 50 | 45.9 |  | 59.2 | 51.6 | 47.3 |  | 61.8 | 48.8 | 41 |  | 61.4 |
| 70/30 | 47.5 | 43.1 |  | 57.4 | 48.3 | 43.8 |  | 59.4 | 43.5 | 37.2 |  | 56.7 |
| 75/25 | 43.9 | 39.3 |  | 53.6 | 43.9 | 39.2 |  | 54.8 | 38.9 | 31.2 |  | 51.4 |

In addition to an ability to absorb and retain relatively large amounts of a liquid, it also is important for an SAP to exhibit good permeability, and, therefore, rapidly absorb the liquid. Therefore, in addition to absorbent capacity, or gel volume, useful SAP fibers also have a high gel strength, i.e., the fibers do not deform after absorbing a liquid. In addition, the permeability or flow conductivity of a hydrogel formed when SAP fibers swell, or have already swelled, in the presence of a liquid is extremely important property for practical use of the SAP fibers. Differences in permeability or flow conductivity of the absorbent polymer can directly impact on the ability of an absorbent article to acquire and distribute body fluids.

Many types of SAP particles exhibit gel blocking. "Gel blocking" occurs when the SAP particles are wetted and swell, which inhibits fluid transmission to the interior of the SAP particles and between absorbent SAP particles. Wetting of the interior of the SAP particles or the absorbent structure as a whole, therefore, takes place via a very slow diffusion process, possibly requiring up to 16 hours for complete fluid the SAP particles. SFC measures the ability of an SAP to transport saline fluids, such as the ability of the hydrogel layer formed from the swollen SAP to transport body fluids. A material having relatively high SFC value is an air-laid web of woodpulp fibers. Typically, an air-laid web of pulp fibers (e.g., having a density of 0.15 g/cc) exhibits an SFC value of about $200 \times 10^{-7}$ cm$^3$sec/g. In contrast, typical hydrogel-forming SAPs exhibit SFC values of $1 \times 10^{-7}$ cm$^3$sec/g or less. When an SAP is present at high concentrations in an absorbent structure, and then swells to form a hydrogel under usage pressures, the boundaries of the hydrogel come into contact, and interstitial voids in this high SAP concentration region become generally bounded by hydrogel. When this occurs, the permeability or saline flow conductivity properties in this region is generally indicative of the permeability or saline flow conductivity properties of a hydrogel zone formed from the SAP alone. Increasing the permeability of these swollen high concentration regions to levels that approach or even exceed conventional acquisition/distribution materials, such as wood pulp fluff, can provide superior fluid handling properties for the absorbent structure, thus decreasing incidents of leakage, especially at high fluid loadings.

Accordingly, it would be highly desirable to provide SAP particles having an SFC value that approaches or exceeds the SFC value of an air-laid web of wood pulp fibers. This is particularly true if high, localized concentrations of SAP particles are to be effectively used in an absorbent structure. High SFC values also indicate an ability of the resultant hydrogel to absorb and retain body fluids under normal usage conditions.

The SFC value of the present multicomponent SAP particles are substantially improved over the SFC value for a standard poly(AA) SAP, as illustrated in the data summarized in Table 11. A method for determining the SFC value of SAP particles is set forth in Goldman et al. U.S. Pat. No. 5,599,335, incorporated herein by reference.

In another test, the free swell rate (FSR) of a present multicomponent SAP particle was compared to the FSR of a standard poly(AA) SAP and 55/45 weight ratio of poly(vinylamine)/poly(acrylic acid) dry particle blend. The FSR test, also known as a lockup test, is well known to persons skilled in the art.

The present multicomponent SAP particles had an FSR (in g/g/sec) of 0.49 and 0.48, for 55/45 weight ratio multicomponent SAP particles made in a KitchenAid mixer and a Brabender extruder, respectively. In comparison, a dry blend had an FSR of 0.10 and a standard neutralized poly(AA) had an FSR or 0.32. Multicomponent SAP particles of the present invention, therefore, have an FSR of greater than 0.35, preferably greater than 0.40, and most preferably greater than 0.45. These data further show the improved ability of the present SAP particles to absorb and retain larger amounts of an electrolyte-containing liquid quickly.

TABLE 11

| Time (min) | Sample 1 (Control) [1] AUL 0.7 psi | Sample 2 (Comparative) [2] AUL 0.7 psi | Sample 3 [3] AUL 0.7 psi | Sample 4 [4] AUL 0.7 psi | Sample 5 [5] AUL 0.7 psi | Sample 6 [6] AUL 0.7 psi | Sample 7 [7] AUL 0.7 psi |
| --- | --- | --- | --- | --- | --- | --- | --- |
| 0 | 0 | 0 | 0 | 0 | 0 | 0 | 0 |
| 5 | 25.3 | 14.8 | 26 | 26.3 | 17.8 | 19.3 | 13.6 |
| 10 | 30.7 | 20.9 | 33.2 | 34.5 | 23.4 | 20.4 | 16.2 |
| 15 | 32.1 | 25.1 | 37.9 | 38.8 | 26.3 | 21 | 17.4 |
| 30 | 33.8 | 31.2 | 43.3 | 44.1 | 29.9 | 20.8 | 17.6 |
| 45 | 34.2 | 34.3 | 45.8 | 45.6 | 31.8 | 21.6 | 19.3 |
| 60 | 34.5 | 36.4 | 47.6 | 46.2 | 32.4 | 21.7 | 20.1 |
| 120 | 35.2 | 40 | 49.1 | 47.6 | 33.6 | 22.3 | 20.5 |
| 180 | 35.2 | 42.3 | 49.7 | 48 | 35.6 | 22.8 | 21.7 |
| SFC [8] | 15 | 115 | 368 | 685 | 707 | 534 | 930 |

[1] Standard, commercial SAP, i.e., neutralized poly(AA), 75% DN, available as A2300, from Chemdal, Corp., Palatine, IL;
[2] Comparative sample containing a dry blend of 55% by weight unneutralized poly(vinylamine) particles and 45% by weight unneutralized poly(AA) particles;
[3] Multicomponent SAP particles, containing 55% unneutralized poly(vinylamine) and 55% poly(AA), prepared in a KitchenAid mixer;
[4] Multicomponent SAP particles, containing 55% unneutralized poly(vinylamine) and 45% poly(AA);
[5] Multicomponent SAP particles, containing 55% unneutralized poly(vinylamine) and 45% poly(AA) as a core-shell granule;
[6] Multicomponent SAP particles, containing 55% unneutralized poly(vinylamine) and 45% poly(AA) as an interpenetrating polymer network;
[7] Multicomponent SAP particles, containing 55% unneutralized poly(vinylamine) and 45% poly(AA) as layers; and
[8] in × $10^{-7}$ cm$^3$sec/g.

The data summarized in Table 11 shows a substantial improvement in AUL at 0.7 psi and SFC for multicomponent SAP particles in comparison to a control SAP and a comparative dry blend of SAP particles. Accordingly, a present multicomponent SAP fiber has an SFC value of at least about 150×10$^{-7}$ cm$^3$sec/g, and preferably at least about 250×10$^{-7}$ cm$^3$sec/g. To achieve the full advantage of the present invention, the SFC value is at least about 350×10$^{-7}$ cm$^3$sec/g, and can range to greater than 1000×10$^{-7}$ cm$^3$sec/g.

The present multicomponent SAP particles also exhibit excellent diffusion of a liquid through and between the particles. Diffusion is measured in a PUP capacity test, which is similar to the AUL test, but the SAP particles are allowed to absorb a fluid on demand. The PUP test is designed to illustrated absorption kinetics of an SAP particle. It is expected that a multicomponent SAP fiber of the present invention has an initial PUP capacity rate of at least 50 g/g/hr$^{1/2}$, and preferably at least 70 g/g/hr$^{1/2}$. To achieve the full advantage of the present invention, the multicomponent SAP fibers have an initial PUP capacity rate of greater than 90 g/g/hr$^{1/2}$, and preferably greater than 100 g/g/hr$^{1/2}$.

The multicomponent SAP fibers also can be mixed with particles of a second water-absorbing resin to provide an SAP material having improved absorption properties. The second water-absorbing resin can be an acidic water-absorbing resin, a basic water-absorbing resin, or a mixture thereof. The SAP material comprises about 10% to about 90%, and preferably about 25% to about 85%, by weight, multicomponent SAP fibers and about 10% to about 90%, and preferably, about 25% to about 85%, by weight, particles of the second water-absorbing resin. More preferably, the SAP material contains about 30% to about 75%, by weight, multicomponent SAP fibers. To achieve the full advantage of the present invention, the SAP material contains about 35% to about 75%, by weight, the multicomponent SAP fibers.

The second water-absorbing resin can be any of the previously discussed acidic resins used in the preparation of a multicomponent SAP. The second water-absorbing resin, either acidic or basic, can be unneutralized (DN=0), partially neutralized (0<DN<100), or completely neutralized (DN= 100). A preferred acidic water-absorbing resin used as the second resin is polyacrylic acid, preferably partially neutralized polyacrylic acid, e.g., DN about 50%, and preferably about 70% up to about 100%. The second water-absorbing resin also can be any of the previously discussed basic resins used in the preparation of a multicomponent SAP. Preferred basic water-absorbing resins used as the second resin are poly(vinylamine) or a poly(dialkylaminoalkyl(meth) acrylamide. Blends of acidic resins, or blends of basic resins, can be used as the second water-absorbing resin. Blends of an acidic resin and a basic resin also can be used as the second water-absorbing resin.

To illustrate the improved absorption properties demonstrated by an SAP material comprising multicomponent SAP particles and particles of a second water-absorbing resin, mixtures of multicomponent SAP particles and partially neutralized (DN=70) polyacrylic acid (poly(AA)) particles were prepared. As used here and throughout the specification poly(AA)(DN=70) refers to a standard, commercial poly(AA) neutralized about 70% to about 80%, and poly (AA)(DN=0) refers to unneutralized poly(AA). The multicomponent SAP particles contain microdomains of poly (vinylamine) dispersed in poly(AA) (DN=0). The poly (vinylamine)/poly(AA) weight ratio of the multicomponent SAP particles was 55/45. The resulting SAP material was tested for an ability to absorb synthetic urine under load at 0.7 psi, in accordance with the previously described method. The results are summarized below:

| wt ratio[1] | AUL 0.7 psi (1 hr.) | AUL 0.7 psi (3 hr.) | SFC ($\times 10^{-7}$ $cm^3$ sec/g) |
|---|---|---|---|
| 100/0 | 26.7 | 27.1 | 14 |
| 75/25 | 30.2 | 30.7 | 26 |
| 50/50 | 36.7 | 37.7 | 72 |
| 25/75 | 40.8 | 42.6 | 189 |
| 0/100 | 43.0 | 46.4 | 787 |

[1]weight ratio of partially neutralized poly(AA) particles to multicomponent SAP particles.

The data presented above shows a substantial improvement in absorption properties achieved by an SAP material comprising a blend of multicomponent SAP particles and particles of a second water-absorbing resin over conventional, partially neutralized poly(AA).

The following Examples 14–17 show SAP materials containing present multicomponent SAP fibers and a second water-absorbing resin.

EXAMPLE 14

The core-sheath multicomponent SAP fibers of Examples 6 and 7, individually, were admixed with a commercial SAP, i.e., ASAP2300™ granules, a 75%–80% neutralized poly (AA) available from Chemdal Corp., Palatine, Ill., until a homogeneous mixture resulted. The resulting mixtures were about 50:50 (w/w) of fibers of Examples 6 or 7 and ASAP2300™.

A typical mixture contained 0.052 g of fiber of Example 6 and 0.050 g of ASAP2300™. The SAP material of Example 14 absorbed 29.7 g/g of synthetic urine after 1 hour under a load of 0.7 psi. In comparison, the fibers of Example 6 absorbed 18.2 g/g and ASAP2300™ absorbed 34.0 g/g, under the identical conditions.

EXAMPLE 15

Similar to Example 14, the fibers of Examples 6 and 7, individually, were admixed with OASIS™ fibers. A typical formulation contained 0.051 g of fibers of Example 7 and 0.050 g of OASIS™, i.e., a 50:50 (w/w) ratio. The SAP material of Example 15 absorbed 20.1 g/g of synthetic urine after 1 hour under a load of 0.7 psi. In comparison, the OASIS™ fibers absorbed 18.9 g/g and the fibers of Example 7 absorbed 26.8 g/g.

EXAMPLE 16

Similar to Examples 14 and 15, the coextruded fibers of Example 12 were admixed with ASAP2300™, i.e., a 50:50 (w/w) ratio. The SAP material of Example 16 absorbed 24.9 g/g of synthetic urine after 1 hour under a load of 0.7 psi. In comparison, the fibers of Example 12 absorbed 28.1 g/g and the ASAP2300™ granules absorbed 34.0 g/g, under identical conditions.

EXAMPLE 17

Similar to Examples 14–16, the coextruded fibers of Example 12 were admixed with OASIS™ fibers. A typical formulation contained 0.05 g of the fibers of Example 12 and 0.051 g of OASIS™ fibers, i.e., a 50:50 (w/w) ratio. The SAP material of Example 17 absorbed 16.0 g/g of synthetic urine after 1 hour under a load of 0.7 psi. In comparison, the fibers of Example 12 absorbed 28.1 g/g and the OASIS™ fibers absorbed 18.9 g/g, under identical a conditions.

EXAMPLE 18

Similar to Examples 14–17, the twisted rope SAP fibers of Example 5 were admixed with ASAP2300™ granules. A typical formulation contained 0.07 g of the twisted rope SAP fibers and 0.11 g of ASAP2300™, i.e., a 40:60 (w/w) ratio. The SAP material of Example 18 absorbed 21.8 g/g of synthetic urine after 1 hour under a load of 0.7 psi. In comparison, the twisted rope SAP fibers of Example 5 absorbed 16.9 g/g and ASAP2300™ absorbed 34.0 g/g under identical conditions.

EXAMPLE 19

Similar to Examples 14–18, the twisted rope SAP fibers of Example 5 were admixed with OASIS™ fibers. A typical formulation contained 0.070 g of the twisted rope fibers and 0.067 g of the OASIS™ fibers, i.e., a 50:50 (w/w) ratio. The SAP material of Example 19 absorbed 14.4 g/g of synthetic urine after 1 hour under a load of 0.7 psi. In comparison, the twisted rope fibers of Example 5 absorbed 16.9 g/g and the OASIS™ fibers absorbed 18.9 g/g, under identical conditions.

EXAMPLE 20

Mixed Bed Fiber

A 50:50 mixture, by weight, of poly(acrylic acid) fibers and poly(vinylamine) fibers was prepared by admixing the fibers. The poly (AA) and poly(VAm) fibers were produced as described in Examples 3 and 4, respectively, and were in the uncured state. The fiber mixture then was passed through a circular core former, which directs the fiber mixture through a sieve and collects the fiber mixture on paper, while under a vacuum, to form a mat. The mat thus formed then was cured, or annealed, for 60 minutes at 125° C. The cured mat was tested for absorbency under a 0.7 psi load, and absorbed 37.6 g/g of synthetic urine after 1 hour and 42 g/g after 4 hours.

In an alternative route, the poly(AA) and poly(VAm) fibers were cured first, either prior to admixing or after admixing, and then the cured fibers were passed through a core former as above. After a final cure of 60 minutes at 125°

C., the fiber mat absorbed 32.9 g/g (of synthetic urine) after 1 hour and 35.3 g/g after 4 hours in an AUL test (under 0.7 psi).

The hydrated mats of Example 20 had very good structural integrity and retained their shape after being removed from the AUL sample pot. The surface of the mat was relatively dry. The hydrated mats did not disintegrate and did not sag to an appreciable degree.

To further demonstrate the improved absorption properties of the present multicomponent SAP fibers, or an SAP material containing the present SAP fibers, the multicomponent SAP fibers and SAP materials were compared to physical blends of fibers and physical blends of a fiber and a granule. The comparative physical blends did not contain multicomponent SAP fibers of the present invention. The following Table 12 summarizes the results of comparative tests on twenty samples, including fibers and SAP materials of the present invention and comparative samples. The tested samples have the following compositions:

| Test Sample | Composition |
| --- | --- |
| 1 | Physical mix[1] of amine fibers of Example 4 and acid fibers of Example 3 (comparative) |
| 2 | Physical mix of amine fibers of Example 4 and poly(AA) granules of Example 1 (comparative) |
| 3 | Physical mix of amine granules of Example 2 and acid fibers of Example 3 (comparative) |
| 4 | Muiticomponent SAP fiber of Example 5 |
| 5 | Physical mix of Test Sample 1 and OASIS ™ fibers (comparative) |
| 6 | Physical mix of Test Sample 1 and ASAP2300 ™ granules (comparative) |
| 7 | Physical mix of amine fibers of Example 4 and reprotonated OASIS ™ fibers (comparative) |
| 8 | Poly(VAm) granules of Example 2 blended with reprotonated OASIS ™ fibers (comparative) |
| 9 | SAP material of Example 14 |
| 10 | SAP material of Example 15 |
| 11 | SAP material of Example 16 |
| 12 | SAP material of Example 17 |
| 13 | Multicomponent SAP fibers of Example 6 |
| 14 | Multicomponent SAP fibers of Example 7 |
| 15 | Multicomponent SAP fibers of Example 12 |
| 16 | Multicomponent SAP fibers of Example 9 |
| 17 | Multicomponent SAP fibers of Example 8 |
| 18 | Multicomponent SAP fibers of Example 10 |
| 19 | Multicomponent SAP fibers of Example 11 |
| 20 | Multicomponent SAP fibers of Example 13 |

[1] All blends were prepared by admixing the solid, dry ingredient until homogeneous; and
[2] OASIS ™ fibers were reprotonated by wetting the fibers with concentrated phosphoric acid. The reprotonated fibers were separated from the acid, then washed with methanol until the methanol filtrate had a constant pH. The reprotonated fibers then were dried at 60° C.

TABLE 12

| Sample[1] | |
| --- | --- |
| 1 | Absorption under 0.7 psi load for 2:1 mix - 14.1 g/g (1 hour) |
| 2 | Absorption under 0.7 psi load for 2:1 mix - 20.6 g/g (1 hour) |
| 3 | Absorption under 0.7 psi load for 1:1 mix - 32.0 g/g (1 hour) |
| 4 | Absorption under 0.7 psi load for 2:1 mix - 13.7 g/g (1 hour) |
| 5 | Absorption under 0.7 psi load for 1:1 mix - 14.3 g/g (1 hour) |
| 6 | Absorption under 0.7 psi load for 1:1 MIX - 21.8 g/g (1 hour) |

TABLE 12-continued

| Sample[1] | |
| --- | --- |
| 7 | Absorption after 1 hour under a 0.7 psi load was 5 g/g fiber/fiber. There was no increase after 3 hours. |
| 8 | Absorption after 1 hour under 0.7 psi was 10.6 g/g, increasing to 17.5 g/g after 3 hours. |
| 9 | Absorption after 1 hour under 0.7 psi was 29.6 g/g, increasing to 31.7 g/g after 3 hours. |
| 10 | Absorption after 1 hour under 0.7 psi was 20.1 g/g, increasing to 22.5 g/g after 3 hours. |
| 11 | Absorption after 1 hour under 0.7 psi was 24.8 g/g, increasing to 27.7 g/g after 3 hours. |
| 12 | Absorption after 1 hour under 0.7 psi was 16.0 g/g, increasing to 19.8 g/g after 3 hours. |
| 13 | Absorption after 3 hours under 0.7 psi was 21.8 g/g. 0 load = 33 g/g after 3 hours. |
| 14 | Absorption after 3 hours under 0.7 psi was 32.8 g/g. 0 load = 28.8 g/g after 3 hours. |
| 15 | Absorption after 1 hour under 0.7 psi was 28.1 g/g, increasing to 38.7 g/g after 3 hours. |
| 16 | Absorption after 3 hours under 0.7 psi was 22.5 g/g. 0 load = 44.6 g/g after 3 hours. |
| 17 | Absorption after 3 hours under 0.7 psi was 24.4 g/g. 0 load = 23.1 g/g after 3 hours. |
| 18 | Absorption after 3 hours under 0.7 psi was 16.34 g/g. 0 psi = 9.12 g/g. |
| 19 | Absorption after 3 hours under 0.7 psi was 22.74 g/g. 0 psi = 20.37 g/g. |
| 20 | Absorption after 1 hour under 0.7 psi was 10.4 g/g, increasing to 14.2 g/g after 3 hours. |

[1] for composition, a poly(VAm) fiber absorbs 14.2 g/g and a poly(AA) fiber absorbs 7.7 g/g.

A present SAP material has an SFC of greater than $15 \times 10^{-7}$ cm$^3$ sec/g, and typically greater than $20 \times 10^{-7}$ cm$^3$ sec/g. Preferred embodiments have an SFC about $30 \times 10^{-7}$ cm$^3$ sec/g or greater, for example, up to about $800 \times 10^{-7}$ cm$^3$ sec/g. In particular, an SAP material containing 25% multicomponent SAP particle and 75% poly(AA)-(DN=70) particles has an SFC of 34.4 cm$^3$ sec/g. A present SAP material also demonstrates an improved initial PUP capacity rate of 45.5 g/g 1 hr$^{1/2}$ for the superabsorbent material. A standard poly(AA)(DN=70) has an initial PUP capacity rate of 40.7 g/g 1 hr$^{1/2}$.

In particular, multicomponent SAP fibers of Example 7 were tested for permeability using the SFC test. Analysis was performed on a 0.1 g test sample under an applied load of 0.3 psi. For synthetic urine, the fibers of Example 7 exhibited an SFC of $603 \times 10^{-7}$ cm$^3$ sec/g. Similarly, for 0.9% saline and artificial blood, the fibers of Example 7 exhibited an SFC of 32 and 4.8 cm$^3$ sec/g, respectively.

The present multicomponent SAP fibers and superabsorbent materials containing multicomponent SAP fibers, (a) have an improved ability to absorb liquids faster, (b) have a better liquid diffusion rate, and (c) have an improved ability to absorb and retain liquids. The present SAP fibers and SAP materials, therefore, are useful in disposable diapers, adult incontinence products, and catamenial devices, for example.

In particular, present day diapers generally consist of a topsheet made from a nonwoven material that is in contact with the skin of the wearer, an acquisition layer below (i.e., opposite the skin of wearer) the topsheet, a core that is below the acquisition layer, and a backsheet below the core. This construction is well known in the industry. The improvements provided by present multicomponent SAP fibers, or superabsorbent material, may permit an acquisition layer to be omitted from a disposable diaper.

In addition, additional test samples, similar to Example 20, were prepared and tested for an ability to absorb synthetic urine. The mixed bed fiber mats contained a weight ratio of either 60/40, 50/50, or 30/70 poly(vinylamine) to poly(acrylic acid), and were prepared identically as set forth above in Example 20. The mixed bed fiber mats were annealed at 125° C. for a time period ranging from 10 to 60 minutes. The ability of the mixed bed fibers to absorb synthetic urine is summarized in Table 13.

TABLE 13

| Weight Ratio of PVAm to PAA Fibers | Cure Conditions | AUL Load (psi) | 1 hr (g/g) | 4 hr (g/g) |
|---|---|---|---|---|
| 50/50 | 125° C. 10 mins | 0 | 68.71 | 65.20 |
|  |  | 0.28 | 34.64 | 46.28 |
|  |  | 0.7 | 32.96 | 45.13 |
|  | 125° C. 20 mins | 0 | 73.57 | 68.40 |
|  |  | 0.28 | 46.68 | 56.43 |
|  |  | 0.7 | 37.59 | 44.35 |
|  | 125° C. 30 mins | 0 | 66.73 | 66.35 |
|  |  | 0.28 | 40.25 | 37.20 |
|  |  | 0.7 | 36.81 | 39.16 |
|  | 125° C. 45 mins | 0 | 62.29 | 59.03 |
|  |  | 0.28 | 41.83 | 39.60 |
|  |  | 0.7 | 31.41 | 36.75 |
|  | 125° C. 60 mins | 0 | 66.53 | 61.97 |
|  |  | 0.28 | 43.54 | 47.22 |
|  |  | 0.7 | 36.05 | 37.39 |
| 30/70 | 125° C. 10 mins | 0 | 53.82 | 47.51 |
|  |  | 0.28 | 41.23 | 48.77 |
|  |  | 0.7 | 27.48 | 39.10 |
|  | 125° C. 20 mins | 0 | 56.19 | 50.67 |
|  |  | 0.28 | 34.77 | 42.56 |
|  |  | 0.7 | 32.31 | 40.03 |
|  | 125° C. 30 mins | 0 | 51.85 | 43.58 |
|  |  | 0.28 | 34.24 | 32.73 |
|  |  | 0.7 | 27.39 | 32.00 |
|  | 125° C. 45 mins | 0 | 49.77 | 45.10 |
|  |  | 0.28 | 37.34 | 44.00 |
|  |  | 0.7 | 32.31 | 31.58 |
|  | 125° C. 60 mins | 0 | 48.75 | 42.39 |
|  |  | 0.28 | 34.34 | 36.47 |
|  |  | 0.7 | 52.59 | 57.73 |
| 60/40 | 125° C. 10 mins | 0.7 | 30.12 | 34.59 |
|  | 125° C. 20 mins | 0.7 | 37.52 | 36.81 |
|  | 125° C. 30 mins | 0.7 | 34.74 | 35.04 |
|  | 125° C. 45 mins | 0.7 | 33.76 | 34.57 |
|  | 125° C. 60 mins | 0.7 | 35.96 | 38.25 |

The mixed fibers of Example 20, and the mixed bed fibers tested in Table 13, showed excellent structural integrity after hydration by synthetic urine, i.e., the mat of mixed bed fibers can be lifted without disintegrating.

In addition, a significant improvement in liquid absorption, both with respect to kinetics and retention, are expected if the standard poly(AA)-(DN=70) presently used in diaper cores is completely replaced by multicomponent SAP fibers, or is replaced by a superabsorbent material of the present invention, i.e., a composition containing multicomponent SAP fibers and a second water-absorbing resin, such as poly(AA)(DN=70).

The improved results demonstrated by the present invention also permit the thickness of the diaper core to be reduced. Typically, cores contain 50% or more fluff or pulp to achieve rapid liquid absorption while avoiding problems like gel blocking. Cores which contain multicomponent SAP fibers acquire liquids sufficiently fast to avoid problems, like gel blocking, and, therefore, the amount of fluff or pulp in the core can be reduced, or eliminated. A reduction in the amount of the low-density fluff results in a thinner core, and, accordingly, a thinner diaper.

Therefore, a diaper core can contain at least 50% of an SAP, preferably at least 75% of an SAP, and up to 100% of an SAP. In various embodiments, the presence of a fluff or pulp is no longer necessary, or desired. In each case, the SAP in the core contains multicomponent SAP fibers, in an amount of about 15% to 100% of the SAP. The remaining SAP can be a second water-absorbing resin, either basic or acidic. The second water-absorbing resin preferably is not neutralized, but can have a degree of neutralization up to 100%. The multicomponent SAP fibers can be admixed with particles of a second water-absorbing resin for introduction into a diaper core. Alternatively, a diaper core can contain zones of multicomponent SAP fibers and zones of a second water-absorbing resin.

In addition to a thinner diaper, the present invention also allows an acquisition layer to be omitted from the diaper. The acquisition layer in a diaper typically is a nonwoven or fibrous material, typically having a high degree of void space, or "loft," that assists in the initial absorption of a liquid. Cores containing multicomponent SAP fibers can acquire liquid at a sufficient rate such that diapers free of an acquisition layers are practicable.

Many modifications and variations of the invention as hereinbefore set forth can be made without departing from the spirit and scope thereof and, therefore, only such limitations should be imposed as are indicated by the appended claims.

What is claimed is:

1. A multicomponent superabsorbent fiber comprising:
   (a) one or more first fibers comprising an acidic water-absorbing resin, and
   (b) one or more second fibers comprising a basic water-absorbing resin, wherein the first and second fibers are twisted together in the form of a braid.

2. The fiber of claim 1 wherein the basic resin comprises a strong basic resin, a weak basic resin, or a mixture thereof, and the acidic resin comprises a strong acidic resin, a weak acidic resin, or a mixture thereof.

3. The fiber of claim 1 wherein the fiber is in the shape of a cylinder having a diameter of about 10 μm to about 1 mm and a length of about 1 mm to about 100 mm.

4. The fiber of claim 1 wherein the fiber is in the shape of a filament having a length:diameter ratio of about 500 to about 10,000:1.

5. The fiber of claim 1 wherein the fiber is surface crosslinked with up to about 10,000 ppm of a surface crosslinking agent.

6. The fiber of claim 1 wherein the basic resin has about 75% to 100% basic moieties present in a free base form.

7. The fiber of claim 1 wherein the basic resin is lightly crosslinked.

8. The fiber of claim 1 wherein the basic resin is selected from the group consisting of a poly(vinylamine), a poly (dialkylaminoalkyl (meth)acrylamide), a polymer prepared from the ester analog of an N-(dialkylamino(meth) acrylamide), a polyethylenimine, a poly(vinylguanidine), a poly(allylguanidine), a poly(allylamine), a poly (dimethyldialkylammonium hydroxide), a guanidine-modified polystyrene, a quaternized polystyrene, a quaternized poly(meth)acrylamide or ester analog thereof, poly (vinyl alcohol-co-vinylamine), and mixtures thereof.

9. The fiber of claim 1 wherein the acidic resin contains a plurality of carboxylic acid, sulfonic acid, sulfuric acid, phosphonic acid, or phosphoric acid groups, or a mixture thereof.

10. The fiber of claim 1 wherein the acidic resin has about 75% to 100% acid moieties present in the free acid form.

11. The fiber of claim 1 wherein the acidic resin is lightly crosslinked.

12. The fiber of claim 1 wherein the acidic resin is selected from the group consisting of polyacrylic acid, a hydrolyzed starch-acrylonitrile graft copolymer, a starch-acrylic acid graft copolymer, a saponified vinyl acetate-acrylic ester copolymer, a hydrolyzed acrylonitrile polymer, a hydrolyzed acrylamide copolymer, an ethylene-maleic anhydride copolymer, an isobutylene-maleic anhydride copolymer, a poly(vinylphosphonic acid), a poly(vinylsulfonic acid), a poly(vinylphosphoric acid), a poly(vinyl-sulfuric acid), a sulfonated polystyrene, a poly(aspartic acid), a poly(lactic acid), and mixtures thereof.

13. The fiber of claim 1 wherein the basic resin comprises a poly(vinylamine), a poly(dialkylaminoalkyl (meth)acrylamide), a poly(vinylguanidine), a polyethylenimine, or a mixture thereof, and the acidic resin comprises poly(acrylic acid).

14. The fiber of claim 13 wherein the poly(dialkylaminoalkyl (meth)acrylamide) comprises poly(dimethylaminoethyl acrylamide), poly(dimethylaminopropyl methacrylamide), or a mixture thereof.

15. The fiber of claim 13 wherein the poly(acrylic acid) resin further contains strong acid moieties.

16. The fiber of claim 1 wherein the first fiber contains at least one microdomain of at least one basic water-absorbing resin.

17. The fiber of claim 1 wherein the second fiber contains at least one microdomain of at least one acidic water-absorbing resin.

18. The fiber of claim 1 wherein the fiber is annealed at a temperature of about 65° C. to about 150° C. for about 20 minutes to about 16 hours.

19. The fiber of claim 1 wherein the first fiber, the second fiber, or both the first and second fibers are surface crosslinked with up to about 10,000 ppm of a surface crosslinking agent.

20. The fiber of claim 19 wherein the first fiber is surface crosslinked with a surface crosslinking agent selected from the group consisting of a polyhydroxy compound, a metal salt, a quaternary ammonium compound, a multifunctional epoxy compound, an alkylene carbonate, a polyaziridine, a haloepoxy, a polyamine, a polyisocyanate, and mixtures thereof.

21. The fiber of claim 5 wherein the surface crosslinking agent is selected from the group consisting of a polyhydroxy compound, a metal salt, a quaternary ammonium compound, a multifunctional epoxy compound, an alkylene carbonate, a polyaziridine, a haloepoxy, a polyamine, a polyisocyanate, and mixtures thereof.

22. The fiber of claim 19 wherein the second fiber is surface crosslinked with a surface crosslinking agent selected from the group consisting of (a) a dihalide or a disulfonate ester having the formula

wherein p is an integer 2 to 12 and Y, independently, is halo, tosylate, mesylate, an alkyl sulfonate ester, or an aryl sulfonate ester;

(b) a multifunctional aziridine;

(c) a multifunctional aldehyde, and acetals and bisulfites thereof;

(d) a halolydrin;

(e) a multifunctional epoxy compound;

(f) a multifunctional carboxylic acid containing 2 to 12 carbon atoms, and methyl and ethyl esters, acid chlorides, and anhydrides derived therefrom;

(g) an organic titanate;

(h) a melamine resin;

(i) a hydroxymethyl urea;

(j) a multifunctional isocyanate; and (k) mixtures thereof.

* * * * *